United States Patent
Wisser et al.

(10) Patent No.: US 12,387,836 B2
(45) Date of Patent: Aug. 12, 2025

(54) CLOUD-BASED INTERACTIVE DIGITAL MEDICAL IMAGING AND PATIENT HEALTH INFORMATION EXCHANGE PLATFORM

(71) Applicant: Actual HealthCare Solutions, East Windsor, NJ (US)

(72) Inventors: Jamie R. Wisser, Cranbury, NJ (US); Peter Byrne, Woodland Hills, CA (US); Fred Rubin, Westport, CT (US); James J. Schulz, Jr., Hamilton, NJ (US); Michael Paglione, Columbus, NJ (US); NayanKumar Jethva, Monmouth Junction, NJ (US)

(73) Assignee: Actual HealthCare Solutions

( * ) Notice: Subject to any disclaimer, the term of this patent is extended or adjusted under 35 U.S.C. 154(b) by 121 days.

(21) Appl. No.: 18/382,684

(22) Filed: Oct. 23, 2023

(65) Prior Publication Data

US 2024/0047044 A1 Feb. 8, 2024

Related U.S. Application Data

(60) Continuation-in-part of application No. 17/863,417, filed on Jul. 13, 2022, now abandoned, which is a
(Continued)

(51) Int. Cl.
*G16H 30/20* (2018.01)
*G06F 16/51* (2019.01)
(Continued)

(52) U.S. Cl.
CPC ............. *G16H 30/20* (2018.01); *G06F 16/51* (2019.01); *G16H 10/60* (2018.01); *G16H 30/40* (2018.01); *G16H 80/00* (2018.01)

(58) Field of Classification Search
CPC ........ G16H 30/20; G16H 10/60; G16H 40/20; G16H 80/00; G16H 15/00
See application file for complete search history.

(56) References Cited

U.S. PATENT DOCUMENTS

| 8,180,654 B2 | 5/2012 | Berkman et al. |
| 8,498,941 B2 | 7/2013 | Felsher |

(Continued)

FOREIGN PATENT DOCUMENTS

| WO | WO-2010067230 A1 * | 6/2010 | ............. G06Q 50/24 |
| WO | 2014063118 A1 | 4/2014 | |

(Continued)

OTHER PUBLICATIONS

Lebre, Rui, Luís Bastião Silva, and Carlos Costa. "A Cloud-Ready Architecture for Shared Medical Imaging Repository." Journal of digital imaging 33.6 (2020): 1487-1498. (Year: 2020).*

(Continued)

*Primary Examiner* — Jason B Dunham
*Assistant Examiner* — Constantine Siozopoulos
(74) *Attorney, Agent, or Firm* — Gearhart Law LLC

(57) ABSTRACT

The system brings together patient data both clinical records and imaging studies from disparate sources to the user workstation or mobile device in real-time and on-demand. In order to do so, the system needs to establish application layer connectivity utilizing HL7 or FHIR and DICOM for imaging. Once a secure connection is established, the system is able to search and retrieve records and present it to end user.

15 Claims, 20 Drawing Sheets

Related U.S. Application Data division of application No. 16/112,203, filed on Aug. 24, 2018, now Pat. No. 11,424,020.

(60) Provisional application No. 62/596,484, filed on Dec. 8, 2017.

(51) Int. Cl.
*G16H 10/60* (2018.01)
*G16H 30/40* (2018.01)
*G16H 80/00* (2018.01)

(56) References Cited

U.S. PATENT DOCUMENTS

| | | |
|---|---|---|
| 8,600,895 B2 | 12/2013 | Felsher |
| 2009/0164474 A1 | 6/2009 | Noumeir |
| 2009/0172773 A1 | 7/2009 | Moore |
| 2013/0054346 A1 | 2/2013 | Sekura |
| 2014/0140637 A1* | 5/2014 | Rachev .............. G16H 40/67 382/305 |
| 2014/0222684 A1 | 8/2014 | Felsher |
| 2016/0162650 A1 | 6/2016 | Newbold et al. |
| 2016/0210408 A1 | 7/2016 | Yu |
| 2016/0314588 A1* | 10/2016 | Harper ................. G06F 16/447 |
| 2016/0357932 A1 | 12/2016 | Morris et al. |
| 2017/0249435 A1 | 8/2017 | Lancelot |
| 2017/0300620 A1* | 10/2017 | Rahme .................. A61B 6/563 |
| 2018/0060496 A1 | 3/2018 | Bulleit |
| 2018/0067986 A1 | 3/2018 | Gupta |
| 2019/0034589 A1 | 1/2019 | Chen |
| 2021/0265041 A1* | 8/2021 | Narayanan ............ G16H 30/20 |

FOREIGN PATENT DOCUMENTS

| | | |
|---|---|---|
| WO | 2017089360 A1 | 6/2017 |
| WO | 2017162544 A1 | 9/2017 |

OTHER PUBLICATIONS

Alyami, Mohammed Abdulkareem, et al. "Managing personal health records using meta-data and cloud storage." 2017 IEEE/ACIS 16th International Conference on Computer and Information Science (ICIS). IEEE, 2017. (Year: 2017).*

* cited by examiner

| Study Access Logs | | | |
|---|---|---|---|
| Viewed On | User | Searched Under | Searched On |
| 2018-08-13 14:45:20 | July24 July24 | JAMIE WISSER | 2018-08-13 14:45:16 |
| 2018-08-12 14:22:09 | Jim Schulz | | |
| 2018-08-12 14:22:08 | Jim Schulz | JAMIE WISSER | 2018-08-12 14:22:01 |
| 2018-08-12 08:22:04 | Jamie Wisser | | |
| 2018-08-12 07:52:12 | Jamie Wisser | | |
| 2018-08-12 07:52:11 | Jamie Wisser | | |
| 2018-08-12 07:48:53 | Jamie Wisser | | |
| 2018-08-12 07:48:52 | Jamie Wisser | | |
| 2018-08-08 16:41:24 | ANDREW SCHECHTER | | |
| 2018-08-08 16:41:23 | ANDREW SCHECHTER | JAMIE WISSER | 2018-08-08 16:41:09 |
| 2018-08-02 13:18:29 | Nayan Jethva | | |
| 2018-08-02 13:18:28 | Nayan Jethva | JAMIE WISSER | 2018-08-02 13:16:17 |
| 2018-08-02 13:15:52 | Nayan Jethva | | |

FIG.4A

ELEMREX™
Bringing Electronic Health Information Together

ADMIN PAGE | SEARCH PATIENT | MY PATIENTS | DOWNLOAD BLANK FORMS | LOGOUT

Search Log Form

| Search String | Searched On | Searched By | First Name | Last Name | Gender* | Replay | DrChrono | HIPPA | Athena | HIPPA |
|---|---|---|---|---|---|---|---|---|---|---|
| john | 2017-07-10 14:14:04 | doctor1@inncretech.com | John | Williams | Male | ▲ | ⊘ | ⊘ | ⊘ | ⊘ |
| john williams Thu Dec 01 00:00 | 2017-07-10 14:14:53 | doctor1@inncretech.com | John | Williams | Male | ▲ | ⊘ | ⊘ | ⊘ | ⊘ |
| sophia | 2017-07-10 14:15:40 | doctor1@inncretech.com | BEOPE,SOPHIA | B | Female | ▲ | ⊘ | ⊘ | ⊘ | ⊘ |
| Anantharaman | 2017-07-10 14:16:16 | doctor1@inncretech.com | ANANTHARAMAN. 78/M | M | | ▲ | ⊘ | ⊘ | ⊘ | ⊘ |
| sophia | 2017-07-15 14:01:29 | doctor1@inncretech.com | BEOPE,SOPHIA | B | Female | ▲ | ⊘ | ⊘ | ⊘ | ⊘ |
| john williams Thu Dec 01 00:00 | 2017-07-21 16:28:39 | doctor1@inncretech.com | John | Williams | Male | ▲ | ⊘ | ⊘ | ⊘ | ⊘ |
| BEOPE,SOPHIA B Sat Sep 17 00:00 | 2017-07-27 12:25:49 | doctor1@inncretech.com | BEOPE,SOPHIA | B | Female | ▲ | ⊘ | ⊘ | ⊘ | ⊘ |
| raul | 2017-07-27 19:14:32 | doctor1@inncretech.com | Raul | R | | ▲ | ⊘ | ⊘ | ⊘ | ⊘ |

FIG.4B

ELEMREX™
Bringing Electronic Health Information Together

| | Cancer | Tumor | Cardiovascular | Pancreatic | Heart | Lung |
|---|---|---|---|---|---|---|
| Study #1 | 1 | | | | | |
| Study #2 | | | | 1 | | |
| Study #3 | | | 1 | | | |
| Study #4 | 1 | | | | 1 | |
| Study #5 | | | 1 | | | |
| Study #6 | | 1 | | | | 1 |
| Study #7 | 1 | | | 1 | | |
| Study #8 | | | 1 | | | |
| Study #9 | | 1 | 1 | | 1 | |
| Study #10 | | | 1 | | | |
| Study #11 | | | | 1 | | 1 |
| Study #12 | 1 | | 1 | | | |
| Study #13 | | | | 1 | | |
| Study #14 | | | | | | |
| Study #15 | | | 1 | | | 1 |

CLOUD-BASED INTERACTIVE DIGITAL MEDICAL IMAGING AND PATIENT HEALTH INFORMATION EXCHANGE PLATFORM

CROSS-REFERENCE TO RELATED APPLICATIONS SECTION

This application is a U.S. Continuation-In-Part Utility Patent Application that claims priority to U.S. Non-Provisional patent application Ser. No. 17/863,417 filed on Jul. 13, 2022 that claims priority to U.S. Non-Provisional patent application Ser. No. 16/112,203 filed on Aug. 24, 2018, now U.S. Pat. No. 11,424,020 that claims priority to U.S. Provisional Patent Application Ser. 62/596,484 filed on Dec. 8, 2017, the entire contents of which are hereby incorporated by reference in their entirety.

FIELD OF THE EMBODIMENTS

The present invention relates to a system and method which brings together patient data from both clinical records and imaging studies from disparate sources to the user workstation or mobile device in real-time and on-demand.

BACKGROUND OF THE EMBODIMENTS

Prior art has revealed the following references:

U.S. Pat. No. 8,180,654B2A teaches a method and system for utilizing indexed electronic patient medical records stored on portable memory devices. Each of the portable memory devices is associated with a patient for electronically storing indexed medical records for the patient from a plurality of care providers. The indexed medical records are sortable or searchable. For each visit to a care provider by a patient, the method includes: (a) accessing the indexed medical records from a portable memory device associated with the patient; (b) automatically generating one or more documents for use during the visit from the indexed medical records; (c) providing medical services to the patient utilizing the indexed medical records and the one or more documents; (d) recording information relating to the medical services on the one or more documents, and loading the information on the portable memory device; and (e) sending delayed information relating to the medical services to a remote server for subsequent downloading by the patient or another authorized person of the delayed information from the server to the portable memory device U.S. Pat. No. 8,498,941B2A teaches a data security apparatus and method for controlling access to records provided within automated electronic databases, each record having an associated set of access rules, comprising: receiving, by a security processor, a request for access to records associated with at least one of an entity, attribute, and datum from a requestor; determining a set of records associated with the requested entity, attribute, or datum, contained in the automated electronic databases; authorizing access to the records within the determined set of records based on compliance with the associated set of access rules; defining an economic compensation rule, satisfaction of which is required for qualification for access to the set of records; selectively permitting access to records in dependence on satisfaction of the compensation rule; communicating the access permissions to the host automated electronic databases; and logging the request for retrieval and a respective access of each record.

U.S. Pat. No. 8,600,895B2A teaches a method of controlling access to records stored within databases, each record having associated access rules, a location identifier, and a content identifier maintained in a centralized index, comprising: receiving a request, communicated from a requestor to a security processor, the request containing a specified content identifier; querying the centralized index to find entries corresponding to the specified content identifier; for each entry, applying the access rules for the record to determine whether the record is accessible; for each accessible record, automatically communicating from the security processor to the database storing the accessible record sufficient information to determine whether it is releasable per a set of native access rules of the database; logically associating the releasable accessible records into a linked set of releasable records; and communicating the linked set of releasable records to the requestor.

U.S. Patent Publication No. 20170249435 teach implementations for providing patient physiological data to a third-party system in near-real-time include determining that a value of a data element within a data source has changed, and determining that the data element is included in a watch list, the watch list including one or more topics, each topic being associated with at least one data element, and in response: providing a data element tuple associated with the data element, and transmitting the data element tuple to the third-party system over a network. Other implementations of this aspect include corresponding systems, apparatus, and computer programs, configured to perform the actions of the methods, encoded on computer storage devices.

None of the prior art solves or teaches the problem of bringing together patient data both clinical records and imaging studies from disparate sources to the user workstation or mobile device in real-time and on-demand.

SUMMARY

According to an aspect of the present invention, a method for gathering and indexing medical records housed on multiple databases is provided. The method includes connecting, using a remote server, to one or more medical records databases, searching, from the one or more medical records databases, one or more medical records for a patient, locating the one or more medical records; retrieving the one or more medical records from the one or more medical records databases, extracting, using a processor, metadata from the one or more medical records, indexing, using the processor, the one or more medical records, using the extracted metadata, and presenting the indexed one or more medical records to a user, in real-time, using a graphical user interface.

It is an object of the present invention to provide the method for gathering and indexing medical records housed on multiple databases, wherein the connecting to the one or more medical records databases further includes utilizing one or more secure connectivity standards selected from the group consisting of: Health Level 7; Fast Healthcare Interoperability Resources; and Digital Imaging and Communications in Medicine.

It is an object of the present invention to provide the method for gathering and indexing medical records housed on multiple databases, wherein the method further includes storing the metadata in one or more storage mediums.

It is an object of the present invention to provide the method for gathering and indexing medical records housed on multiple databases, wherein the indexing the one or more medical records further includes using data selected from the group consisting of: patient data; doctor data; and relationship data.

It is an object of the present invention to provide the method for gathering and indexing medical records housed on multiple databases, wherein the one or more medical records includes medical imaging records.

It is an object of the present invention to provide the method for gathering and indexing medical records housed on multiple databases, wherein the one or more medical records databases are selected from the group consisting of: electronic medical records systems; and picture archiving and communicating systems.

It is an object of the present invention to provide the method for gathering and indexing medical records housed on multiple databases, wherein the method further includes searching the indexed one or more medical records, using the graphical user interface.

It is an object of the present invention to provide the method for gathering and indexing medical records housed on multiple databases, wherein the method further includes presenting, to the user, using the graphical user interface, a patient summary of the patient, wherein one or more users may view the indexed one or more medical records.

It is an object of the present invention to provide the method for gathering and indexing medical records housed on multiple databases, wherein the patient summary includes information selected from the group consisting of: patient demographics; allergies; medications; immunizations; patient problems; patient social history; medical equipment; family history; vital signs; physical findings; encounters; plan of care; procedures; and results.

It is an object of the present invention to provide the method for gathering and indexing medical records housed on multiple databases, wherein the method further includes inputting, using the graphical user interface, medical commentary for the patient, the medical commentary being saved to the indexed one or more medical records.

According to another aspect of the present invention, a system for gathering and indexing medical records housed on multiple databases is provided. The system includes a remote server configured to connect to one or more medical records databases, search, from the one or more medical records databases, one or more medical records for a patient, locate the one or more medical records, and retrieve the one or more medical records from the one or more medical records databases. The system further includes a processor, configured to extract metadata from the one or more medical records and index the one or more medical records, using the extracted metadata. The system additionally includes a graphical user interface configured to present the indexed one or more medical records to a user, in real-time.

It is an object of the present invention to provide the system for gathering and indexing medical records housed on multiple databases, wherein the remote server, when connecting to the one or more medical records databases, is further configured to utilize one or more secure connectivity standards selected from the group consisting of: Health Level 7; Fast Healthcare Interoperability Resources; and Digital Imaging and Communications in Medicine.

It is an object of the present invention to provide the system for gathering and indexing medical records housed on multiple databases, wherein the system further includes one or more memory storage mediums, configured to store the metadata.

It is an object of the present invention to provide the system for gathering and indexing medical records housed on multiple databases, wherein the processor, when indexing the one or more medical records, is further configured to use data selected from the group consisting of: patient data; doctor data; and relationship data.

It is an object of the present invention to provide the system for gathering and indexing medical records housed on multiple databases, wherein the one or more medical records includes medical imaging records.

It is an object of the present invention to provide the system for gathering and indexing medical records housed on multiple databases, wherein the one or more medical records databases are selected from the group consisting of: electronic medical records systems; and picture archiving and communicating systems.

It is an object of the present invention to provide the system for gathering and indexing medical records housed on multiple databases, wherein the graphical user interface is further configured to enable the user to search the indexed one or more medical records.

It is an object of the present invention to provide the system for gathering and indexing medical records housed on multiple databases, wherein the graphical user interface is further configured to present the user with a patient summary of the patient, wherein one or more users may view the indexed one or more medical records.

It is an object of the present invention to provide the system for gathering and indexing medical records housed on multiple databases, wherein the patient summary includes information selected from the group consisting of: patient demographics; allergies; medications; immunizations; patient problems; patient social history; medical equipment; family history; vital signs; physical findings; encounters; plan of care; procedures; and results.

It is an object of the present invention to provide the system for gathering and indexing medical records housed on multiple databases, wherein the graphical user interface is further configured to enable the user to input medical commentary for the patient, the medical commentary being saved to the indexed one or more medical records.

BRIEF DESCRIPTION OF THE DRAWINGS

The foregoing and other features of embodiments will become more apparent from the following detailed description of embodiments when read in conjunction with the accompanying drawings. In the drawings, like reference numerals refer to like elements.

FIGS. 4A-4B illustrate a search history flowchart of the present invention, as illustrated in FIG. 4A for PACS search log, or EMR search log as illustrated in FIG. 4B, in accordance with an embodiment of the invention.

FIG. 13 illustrates a clinical record and image service screenshot, in accordance with an embodiment of the invention.

FIG. 14 illustrates the Real-time collaboration tool, in accordance with an embodiment of the invention.

DETAILED DESCRIPTION OF THE EMBODIMENTS

Figure 1:
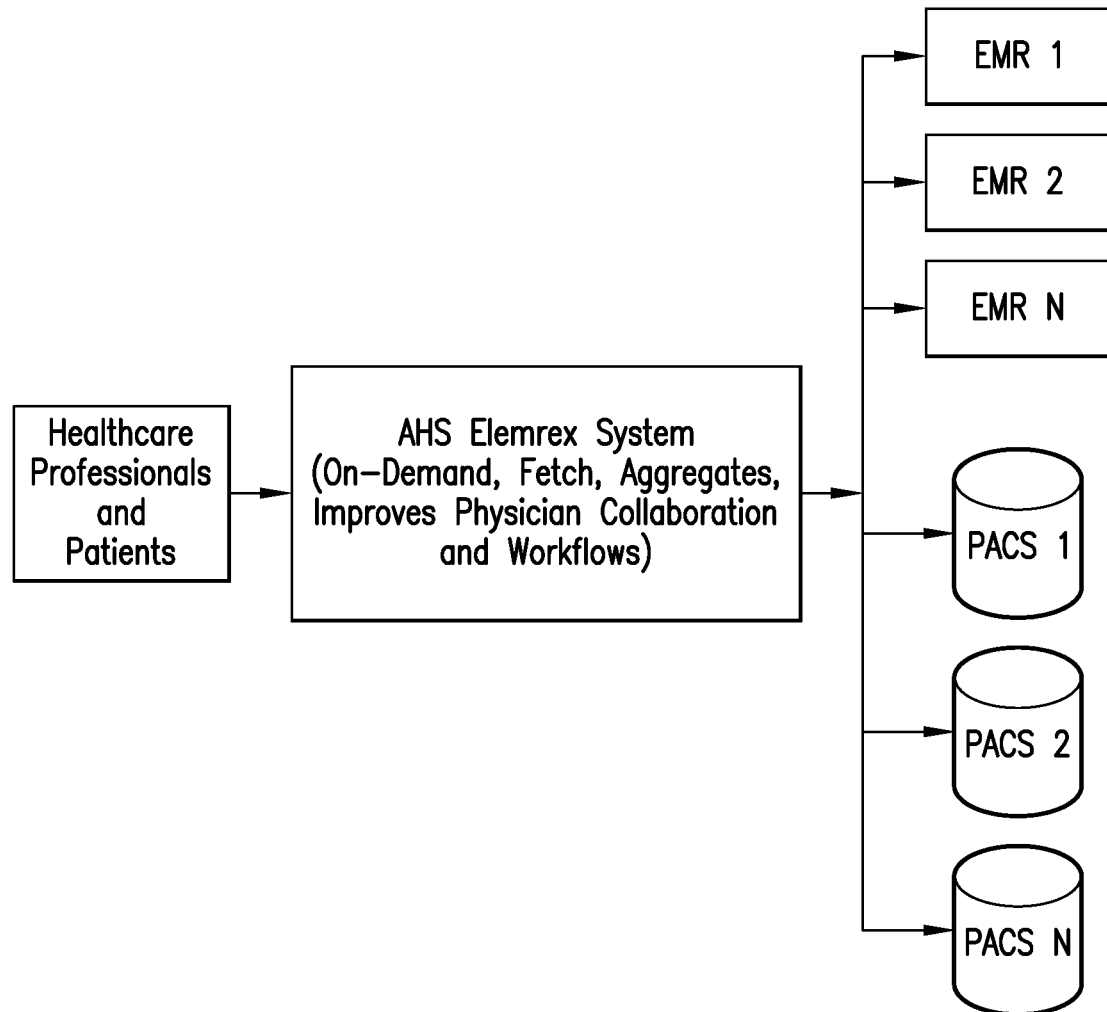
FIG. 1 illustrates a cloud-based interactive digital medical imaging and patient health information exchange system, in accordance with an embodiment of the present invention.

Reference will now be made in detail to the description of the present subject matter, one or more examples of which are shown in figures. Each example is provided to explain the subject matter and not a limitation. Various changes and modifications obvious to one skilled in the art to which the invention pertains are deemed to be within the spirit, scope and contemplation of the invention.

The present invention's system and method solves the problem of bringing together patient data from both clinical records and imaging studies from disparate sources to a user workstation or mobile device in real-time and on-demand. In order to do so, the system needs to establish application layer connectivity utilizing Health Level 7 (HL7) or Fast Healthcare Interoperability Resources (FHIR) and Digital Imaging and Communications in Medicine (DICOM) for imaging. Once a secure connection is established, the system is able to search and retrieve records and present it to an end user.

While doing so, the system stores metadata and indexes patient and doctor data as well as relationship data to improve the effectiveness and efficiency of doctors on a daily basis, thereby saving time for healthcare professionals and improving patient outcomes. The present invention helps in addressing challenges faced by healthcare professionals such as long waiting times for receiving patient's medical records from diverse Picture Archiving and Communicating Systems (herein PACS) and Electronic Medical Record (herein EMR) systems, inefficiencies in receiving tests and reports, and delays in patient care which may lead to bad outcomes.

The present invention uses ELEMREX™, which creates the world's first MODL (Medical Organic Digital Library) and PPM (Patient Provider Matrix). Digital medical imaging is commonly ordered for nearly every person evaluated throughout the healthcare system, being ordered and reviewed by nearly every type of medical specialist. Depth of information contained and interpreted within each study, Radiologist interpretation, and secondary ordering physician review most knowledgeable of the patient's clinical condition, is being designated by the system as the foundation for ELEMREX™'s integrated patient health information library, or MODL.

The present invention implements a system and method to fetch patient records from multiple remote PACS and EMR systems in real-time, -on-demand, and stores, indexes and organizes it for improved physician workflow, physician collaboration with the goals of saving time and cost for the patient and physicians as well as improving better treatment outcomes. According to an embodiment, one or more of the processes of the present invention are performed by one or more processors coupled to one or more electronic devices and/or servers. According to an embodiment, data stored according to the present invention is stored on one or more memory storage devices that are coupled and/or remote from the one or more electronic devices and/or one or more servers.

FIG. 1 illustrates the system of the present invention. According to an embodiment, the system stores the following information, provided by healthcare professionals and patients and using the ELEMREX™ system:

Connection configuration for each EMR (e.g., EMR 1, EMR 2, . . . , EMR N).

Connection configuration for each DICOM or PACS server (e.g., PACS 1, PACS 2, . . . , PACS N).

Patient Entity (master record in the present invention) is related to multiple EMR-Patient and/or multiple DICOM-Patient, one for each remote data source.

Each EMR-Patient/DICOM-Patient can be related to multiple records or studies.

Search Logs (described in Search log section).

Patient Search Query and Results: The present invention's system can query and search patient records from 3rd party PACS and EMR systems utilizing FHIR, HL7 Gateway or 3rd party Representational State Transfer (REST) Application Interfaces (API's). Depending on the interface with 3rd party system different data models are obtained and then further normalized to the system's defined standard data model. To utilize this, the system is first configured to connect with remote PACS servers using VPN or gateway connectivity, and EMR systems using API keys or direct access. Upon which, a physician can search for patient records across multiple Electronic Health Records (EHR) Systems by parallel making queries to multiple systems and aggregating the responses in real-time, using one or more graphical user interfaces. According to an embodiment, the system connects to the EMRs and PACS servers using one or more remote servers.

The querying process identifies the medical record number (MRN) of the desired patient. An MRN number is a unique ID by which a patient is identified on both PACS and EMR systems. The present invention's system generates a unique ID for each PACS+MRN, EMR+MRN combination such that the patient can be uniquely identified in the system using the unique ID, or master patient identifier number, as part of a Master Patient Index (MPI). Searching of patient and fetching digital medical imaging and patient clinical records can be a single step or multiple step process depending on the PACS or EMR system that the present invention's system interfaces with. In some systems, the present invention's system first searches for patients and get the MRN from remote PACS or EMR systems along with patient demographics which is used to identify the correct patient and then the present invention's system utilizes the MRN-ID to retrieve digital images or clinical records for the patient from the PACS or EMR in which they respectively reside. The Master Patient index has in part been created because, in some instances, duplicate records on remote EMR's or duplication created because of records about the same patient from multiple PACS or EMR systems are encountered. This Master Patient Index is discussed below.

In the present invention's system, the physician initiating the search makes the final determination about which is the correct patient "John Doe" which was searched. Similar to a Facebook (FB) Like or LinkedIn Thumbs up, a Radiologist, for example, clicks on a "Radiologist confirmed" icon, or a reviewing physician of any specialty clicks on "Correct/Save and Close" icon to validate patient health data matching. This allows for the present invention's system to be manually improved over time by the physicians themselves. This is utilized by the present invention's system to link multiple patient records from different PACS or EMR systems into one patient manually.

Figure 2A:
FIGS. 2A-2B illustrate an aggregated view for the combining of PACS digital imaging studies (FIG. 2A) or clinical records (FIG. 2B) based on multiple dimensions, in accordance with an embodiment of the invention.
Figure 2B:

Clinical Summary—Once a provider has located a patient record to review, they can click into a clinical summary for that patient. This summary includes several data points:
  Patient demographics,
  Allergies,
  Medications,
  Immunizations,
  Patient Problems,
  Social history,
  Medical equipment,
  Family history
  Vital signs,
  Physical findings,
  Encounters,
  Plan of care,
  Procedures,
  Results, Aggregated View: Clinical summaries from multiple EMR systems are combined in a single view. This aggregated view will not only show clinical records but also medical imaging files like X-Ray, CT, MM, and sonogram content. This aggregated view allows for the combining of clinical records based on multiple dimensions as is illustrated in FIGS. 2A and 2B. Aggregation is performed for the same sub-category of clinical record e.g., Problem Name is combined with Problems from multiple records and likewise, Medication or Allergies, as clinical categories. As illustrated in FIGS. 2A and 2B, the aggregate view can be organized based on chronological order, by EMR or PACS system, diagnosing physician to enable the provider utilizing the system to easily identify patterns and previous diagnostic behaviors and eliminate certain paths or prioritize certain treatment paths. As illustrated in FIG. 2A, current digital medical imaging aggregation is implemented for imaging study type, PACS source, ordering physician, date, time stamping of study performing and each physician review, as well as identifying the reviewing physician. As illustrated in FIG. 2B, EMR integration includes problem name, problem start date, EMR source, allergy list, allergic reaction, medication list, date, time stamping and name of the data entering physician, as well as date, time stamping and identity of reviewing physicians.

Figure 3A:
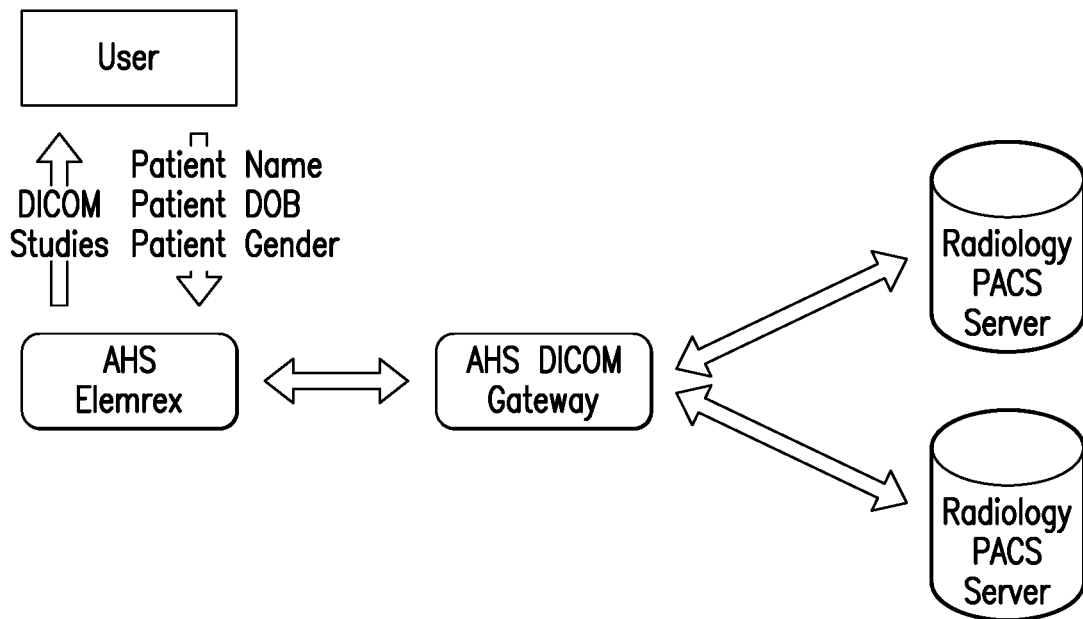
FIGS. 3A-3B illustrate a PACS image data relationship (FIG. 3A), or from EMR sourcing (FIG. 3B) in accordance with an embodiment of the invention.
Figure 3B:
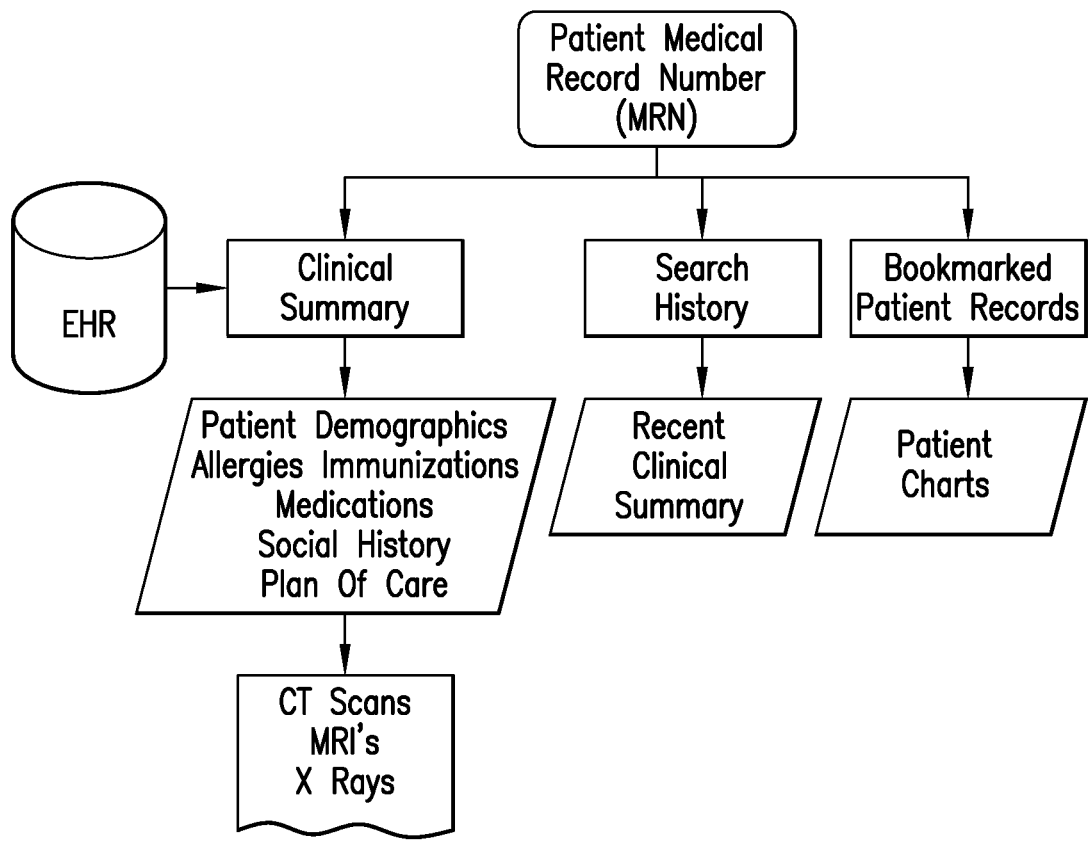

FIG. 3 illustrates a data relationship and is broken down into PACS (FIG. 3A) and EMR (FIG. 3B) fetch and search integration. FIGS. 4A-4B illustrate the Search History of the present invention (FIG. 4A for PACS and FIG. 4B for EMR data).

The present inventions system offers a "save search" function, which essentially stores the search string and the clinical record, which has been considered to be the correct match. If a provider wants to quickly find a recently viewed PACS search log, as illustrated in FIG. 4A, or patient clinical summary, the provider can review the EMR search history, as illustrated in FIG. 4B, to locate the clinical summary view without having to submit the original search parameters and go through the process of ensuring that they are viewing the correct clinical records from a multitude of clinical records which can be obtained for any search string. Search history can be shared with other doctors and reviewing physicians can access the search history performed by other doctors. A search log may contain many pieces of information such as:
  Original search string,
  Timestamp of the search,
  Originator of search,
  Viewer of the search, and
  Patient information.

Replay: The present invention's system allows users to store snapshot data as to when a search was performed and reviewed as well as view it during replay. In addition, during replay, the system allows a user to fetch the most recent data from connected PACS or EMR systems. This gives the reviewing doctor a clear idea on why a particular diagnosis/prognosis or care plan was chosen by a previous doctor and review what data was available at a previous point of time. Each instance of search and view allows taking of a snapshot of the data.

Diff—During replay of clinical records a "diff" can be calculated to identify what part of patient's clinical information has changed. For replay of PACS image reviews, the system archives physician mark-ups and annotations that incorporate the physician clinical familiarity with a patient, clinical experience and fund of knowledge to analyze and record data identifying variations between imaging studies for a particular patient. This takes advantage of physician comparing and contrasting skills when identifying and annotating differences between imaging studies, and integrates what we have termed an 'organic' alternative to image artifact, focus, magnification, intensity and patient positioning issues that currently plague digital image mapping algorithms. An additional benefit of the organic/digital interactivity unable to be captured using digital mapping algorithms is the Physician's ability to interpret different imaging modalities and studies of the same anatomical abnormality to enhance physician interpretation of any particular study's findings.

Physician interpretation of EMR data includes identifying newly added entries e.g., a new Problem or Medication, and provides a method for physician interpretation and annotation entry to the patient's searched records. This dynamic 'organic' interface allows for the incorporating of a clinician's familiarity with a patient, diagnostic prioritizing, treatment and responses within the system's integrated clinical database for each queried patient. Modified entries can be further analyzed for changes, and in case of numerical data, a percentage change, positive or negative change can be calculated.

Since the present invention's system can replay as well as diff past searched records, it can generate triggers or emails to treating doctors based on "time" (periodicity), based on changes (percentage change beyond a threshold), or based on matching of certain attributes which can be defined using a rile based system. These alerts and triggers are based on or derived from changes in records.

The system allows for multiple criteria to be entered and viewed in the search logs as well as gives the user the ability to search or sort as well as filter search logs. In the present invention's system, the reviewer gets an option to narrow down the searched logs based on originating doctor, patient demographics, clinical data, viewing doctor and data source. By specifying age, date of birth, racial background, gender and a time-range, the reviewer can further drill down the list of search log entries and isolate patient information or ordered imaging studies while reviewing. The system allows for filtering and sorting of the transaction log by the doctor who creates the search log, the information originating doctor, and by the source EMR or PACS systems from which the data or image has been pulled. This can be achieved by filtering of data on the client side or modifying the query on search log entries or applying filters after fetching replay data from EMR systems.

Medication Analytics: Aggregate analytics around total number of problems, medication, allergies, as categorical examples, can be performed as well as association mining can be done by problem about which demographics, medication, allergies and additional patient data categories such as lab results can be determined, which medication was mostly used with what combination of problems/allergies or other treatment modalities for clinician review (See current invention application for patient Clinical Trial recruitment and real time patient journey monitoring below). For a given problem, the system and methods can pull the records related to that problem and provides analytics as to what medications were prescribed. For example, if the search term is "abdominal pain", all Protected Health Information (PHI) records that contain "abdominal pain" as a described problem are retrieved first. For each medical record with "abdominal pain" listed as the problem, an analytics algorithm will look at what medications were prescribed, and count the number of occurrences of each unique medication across the entire dataset, and will finally compute and present the aggregate metrics for medications prescribed, such as "70% of prescribed medication for 'abdominal pain' include 'Mefoxin'. In order to speed up the process of obtaining medication insights, the system can choose to skip processing the entire dataset, and can instead obtain a random sample of patient's records matching the search criteria, and compute a statistical estimate of the metrics, within a particular confidence level.

Meta-data showing with Search Logs and Replay: The search log functionality returns a list of records for which the reviewer can view derived statistics. Records for an entire range of lab and imaging tests performed for each listed patient is accompanied by percentage numbers identifying how many within the list had those test. For example, the search log may be stated as 50% had abdominal CT scans, 100% had serum Amylase testing, and 70% had urinalyses, etc. This allows the physician to understand the uniqueness of case and potentially availability of other cases with varying outcome to refer to or other physicians to consult with.

In another embodiment of the invention, transactions listed when a record is pulled, highlights those transactions that were conducted within a defined time window (e.g. 3 months from the imaging study date), but then color codes to highlight any of the remaining listed transactions outside the defined window that match one or more criteria like same source pull, patient's race, gender, age, or a weighted sum of all demographic and clinical factors. This weighted sum can be defined by the physician during search or can be a pre-configured parameter.

Alerts based on Search History Views: Each time an inquiring reviewing Doctor creates a new reviewing transaction, the treating Doctor for that patient can be alerted. The treating doctor chooses that feature, allowing a Physician who actually treats the patient to become aware and provides access for him or her to review any new, unsolicited commentary that may be added by any reviewing doctor to the patient record that the treating doctor can then be alerted to and choose to review. This can be implemented in an anonymized, or patient identifying scrubbed way, as well (See Medical Organic Digital Library (MODL) below).

Furthermore, implementation of such a system may utilize a subscription/notification subsystem such that a user of the system can subscribe to certain events happening triggering system notifications, for example, using a message broker. Each event is published to the message broker, which is maintaining the clinician's subscription feature choices, and distributes the events to all preferring subscribers.

Bookmarked Patient Records: Providers may want to ensure that specific, selected patient aggregated views are available for frequent review without needing to search for them each time by clicking and adding favorites to a 'My Patient List" search history. A provider can bookmark a set of digital medical images or clinical summary while viewing and the patient chart will appear in the provider favorites until it is removed.

Inconsistency Resolution and Alerting: The present invention utilizes rule-based engine and a statistical threshold based system to alert the viewer with any discrepancies and irregularities. For example, if the standard deviation of a measurement or a set of readings is higher or lower than the defined threshold, the doctor selecting this feature will be alerted. It could be also based on elapsed time as a criteria. The system processes all data from each record by category and statistically identifies and highlights variations with respect to similar records, which it then alerts and identifies a subscribing physician of any discrepancies and creates statistical confidence percentage values that are then displayed in any number of ways, i.e., distribution bell shaped curves, pie charts, bar charts, x/y/z scattered data points, whichever the reviewing format the reviewer prefers.

In an alternative embodiment of the present invention, an electronic integration of untapped physician fund of knowledge and clinical experience to build the world's first interactive "Virtual Bedside" and organic/digital patient care decision AI technology is described herein.

Figure 5:
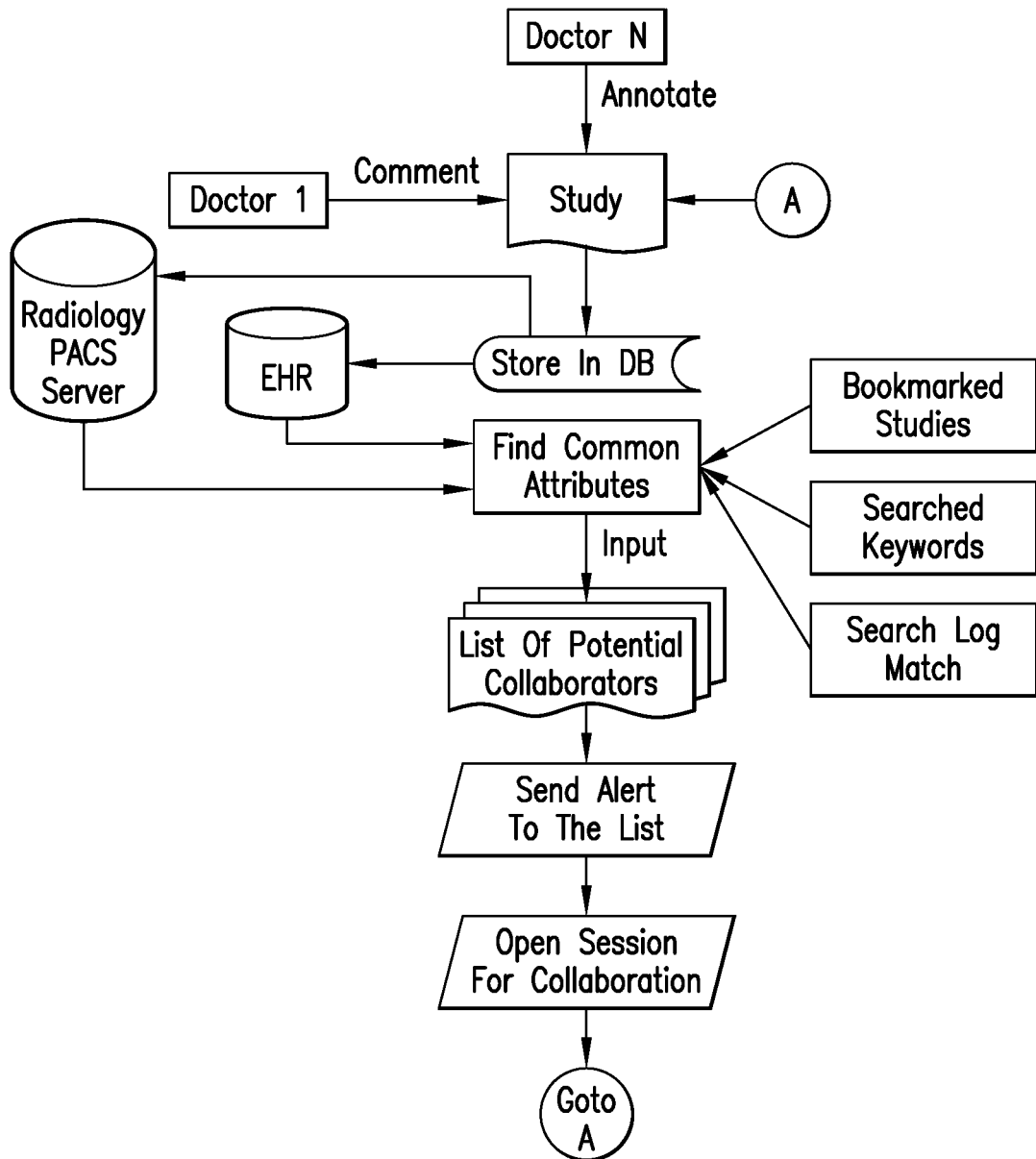
FIG. 5 illustrates a flowchart of a session for a collaborative platform for doctors, in accordance with an embodiment of the invention.

FIG. 5 illustrates a flowchart of a session for a collaborative platform for doctors who could become potential key collaborators while working on individual or group studies based on the metric data gathered while they interact with the studies displayed by the PPM. Various logs are gathered when someone interacts with the system for example keyword patterns searched, bookmarked studies and the logs of patient data are stored for the individual physicians which hold the potential to share or collaborate on solving the case while bringing in diverse expertise. The matching algorithm produces a list of potential collaborators as a unique mix in which various components of ELEMREV™ are collated to determine the group. This in turn promotes higher and more relevant collaboration within the organization. In this scenario, a comprehensive collaborative diagnosis can help residents connect with the primary healthcare provide for the patient who can also connect to a physician specialist based on the automated session created from a potential collaborators list. So when multiple doctors comment/annotate or search for the patient using keywords or name attributes the system gathers this information to be processed later. The system will develop inference rules from the uniquely storing data for three metrics, such as, keywords searched and studies found corresponding to them, and a unique search log that lists the physicians and collaborators for a particular patient's imaging study. Based on these stored metrics a list of key potential collaborators is generated to create a session. The alert based system kicks in and notifies the members of the list for a potential to collaborate based on their activity footprint within the system. After which, the system opens up a session that gives the platform for the members to share their skills and knowledge which boosts collaborative diagnosis and management decision making.

Based on automatic identification of clinical records being viewed or search logs being replayed, suggestion for collaboration made by the system can be selected as a subscription feature. Furthermore, the collaboration itself may involve multi-channel linking through video sharing, screen sharing, chat room, or annotations on shared imaging study snapshots. Each collaboration session can be stored as a transaction on the system, which can be updated to restore original data. Each collaboration can be created in multiple ways through auto-invite, on-demand invite and being pre-invited, utilizing any channel like video, screens sharing or chat room based collaborating within the "Virtual Bedside" functions.

If two Doctors, based on auto-suggestion or invited collaboration, want to look at an imaging study or EMR data that has been pulled, in real time, the first pulls the image as a new transaction; the 2nd goes into the system, clicks on Doctor 1's transaction, and both can be viewing an imaging study from the source at the same time, each, however, through their own transaction. Any number of participants can engage in real time common viewing through initiating independent transactions, seamlessly making comments or additions, mixes and matches separately from the actions of other participants that are commonly viewable by all participants in real time. Each doctor's engagement is independently cataloged as a distinct entry into a common transaction log categorized for that patient's imaging study or common PHI data set being reviewed. If Doctor 1 reviews Doctor 2's annotations and then makes additions to the first's, a new transaction log entry is created to distinguish any changes and preserve the integrity of the original transaction entry. In this way the current invention provides reviewable physician interactivity logging that extends beyond the confines of current EMR or PACS physician interactivity limitations.

The present system allows for the pulling live images and manipulating them in real time, being able to commonly view and share from within the system on one screen, leaving the original imaging study or pulled PHI untouched and in place, at the source. In this way the system's data aggregation:

Leaves responsibility of transacting the most recent, up to date information within routine day to day use of original source servers, Takes advantage of centralized data processing while reducing security or corruption risk by leaving data it the original source, unaffecting local use.

Introduces interactive image and PHI manipulating but preserves the integrity of the original medical record.

There is creation of a health information exchange system that, through its use, organically builds the world's first physician/patient data learning environment that will transform health information into a clinical medical/organic digital library with the acronym "MODL" of current, real time data that is accessible and directly applicable to aid Physicians in their clinical practice. The larger picture is the creation and organization of big data that occurs with routine daily system use that stratifies, classifies, statistically analyzes and presents in a way that collates commonalities for physicians to access and base current treatment decision making upon for like patient cases they are currently dealing with in the present. This fundamentally reestablishes the paradigms of scientific methodical gathering, analyzing, collating of information after management has been rendered, the inherent antiquated nature of such gathered and organized information, and brings routine daily technology use into play as information is routinely analyzed and integrated when it is gathered for timely application in real-time patient care rendering by physicians:

The present invention's system and method is described below:

a. health information exchange logging that allows for replaying of transactions that leave original PACS images or EMR information alone, within its original source, but enables clinicians to access and share the information in a dynamic, interactive environment that will store the sequencing of data acquisition, visualization, highlighting, commenting and collating based upon physician interpretation and commentary to create:

transformative health record databases that integrate:
  L information itself,
  ii. source of information,
  iii. what information was accessed, looked at and commented upon in what sequence, and by whom,
  iv. the timing and sequencing of practitioner commenting and collating of common phrases or terms used or cited in official reports interpreting studies that were performed creates a matrix of connectivity for in depth decision tree annotating, what is called $4^{th}$ dimensional health record keeping, that includes:

b. patients and provider/facility listings where information is gathered and where sequential accessing, reviewing and interpreting of the information occurs and wherein three dimensional management matrices upon which statistics can be gathered and integrated into common categories is able to be illustrated.

c. Once common data is organized by commentary or report common phrases and words, statistical breakdowns of commonalities from within all commentary-originated titles are technically collated and organized to create further analysis. PHI pulled by physicians when looking at accessed digital imaging studies provides a broad palate of information that can be crawled for commonalities and statistical breakdowns. Example: Of the 100 CT scans of the abdomen that have been collated with the Radiology reading and physician commentary for a common phrase, pancreatic cancer, of the viewer identifier scrubbed, but system matched PHI records for these patients that were pulled by the Physicians during their patient information exchanges, what is the statistical breakdown of Amylase enzymatic levels of all 100 patients. If only 50 patients had their Amylase levels pulled, how do they relate to:
1. The tumor size as measured by clinicians when they provided these additional inputs when reviewing the study.
2. What is the average measurement that correlates with the stratified amylase levels?
3. What types of specialists' accessed data and how frequently for each of these patients?
4. How many cumulative hospital days were logged and pulled into the system for each of these 100 patients?
5. How many out-patient office visits within a certain time period?
6. How many patients with these lab and imaging findings had an operation within what time period of these findings being made?
7. What was the percentage of patients that were operated upon that were able to be successfully resected vs. palliated?
8. What was the length of stay comparing those that were discharged having been resected vs. those who were treated with palliative operations?
9. What was the average time interval to obtain a post-op CT scan for assessing post-operative recurrence or tumor growth in resected vs. palliative treated patients, respectively?
10. At what time interval was the first post-op CT scan done, on average, and what was the tumor size measured by the specialist and entered into the system if palliatively treated?

Figure 6:
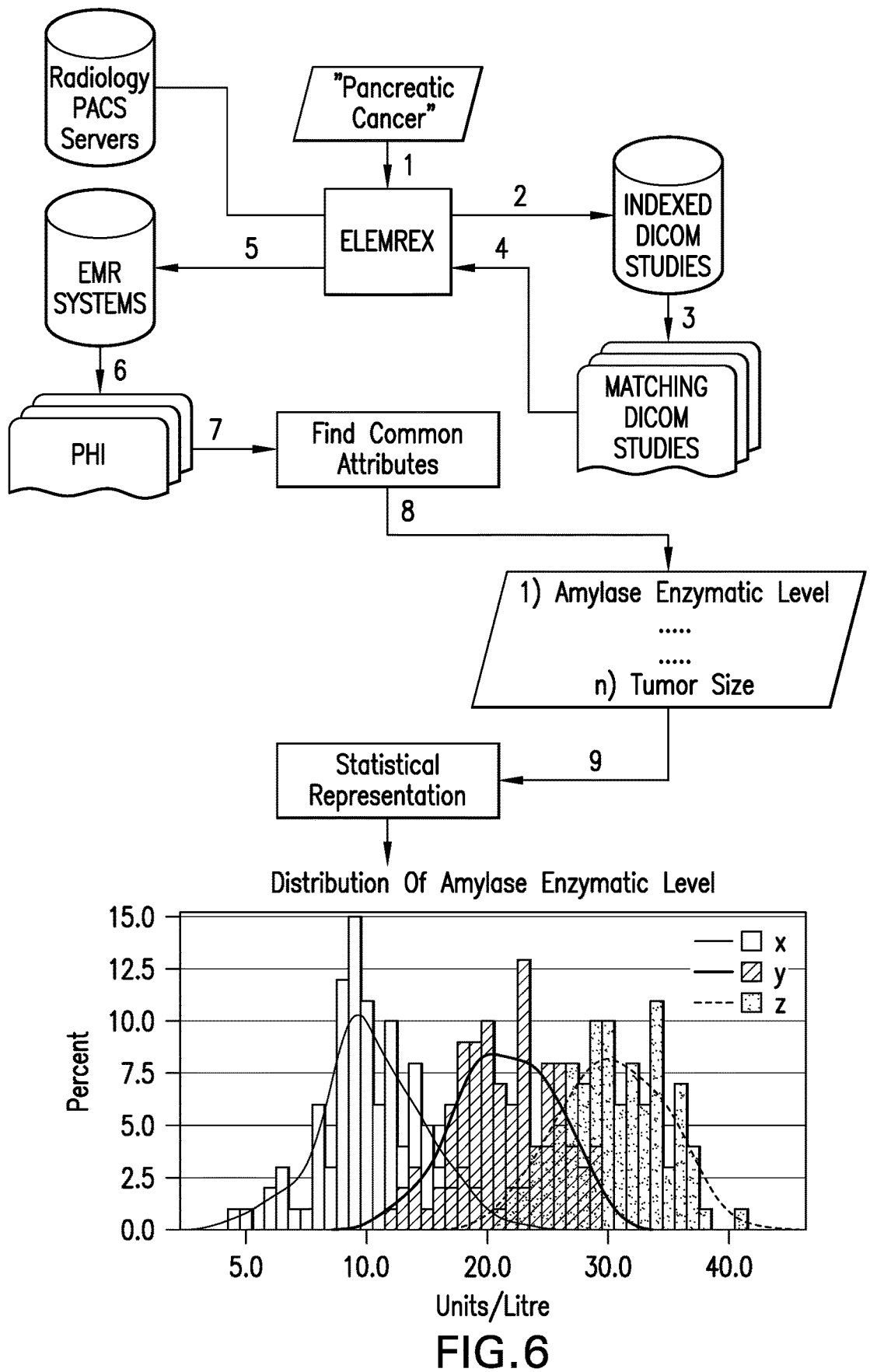
FIG. 6 illustrates a search query flowchart, in accordance with an embodiment of the invention.

FIG. 6 illustrates when a physician enters the search query "Pancreatic Cancer". The system (herein referred to as ELEMREX™ and described below) searches through all of the indexed DICOM studies to find the ones that are associated with the tag "Pancreatic Cancer" as entered by the user. Using metadata from the studies, ELEMREX™ queries multiple EMR systems to retrieve consolidated Patient Health Information of the patients whose studies were returned. Using the PHI records, ELEIVIREX™ finds out the attributes that are common to all the records (such as "Amylase Enzymatic Level", "Tumor Size", etc.) and uses those attributes to generate descriptive and inferential statistics.

Once these types of data point questions are inputted by subscribing physicians or resource specialists, every time a patient has an abdominal CT scan with a commentary or Radiology report stating pancreatic cancer, the artificial intelligence (AI) system will enable the system to add the patient to the group of 100 to increase the denominator, and intrinsically search and categorize each and every subsequent patient according to the data queries that have been listed. This exemplifies that, with each use of the present invention's technology and adding of an imaging study, it adds to the system's big data acquisition, but is able to, in real-time, on a case by case basis, update, categorize and stratify the newly added imaging study and commentary, that creates summary information from which patterns of activity can be reported on. A new practitioner with a patient with Pancreatic CA can then access the system and see the patterns of diagnosis, practice, referrals, commentary, measurements, treatments rendered, and outcome as the technology stratifies information and transforms information into patterns of patient management that clinicians can apply to their current daily practice, or as ongoing, real-time evolving reference source for education, and further analytical use outside the system. According to an embodiment, the invention's ID scrubbed patient management analytics developed through routine daily system use provides a foundation for up-to-date patient care pathway generation that becomes a separate, sellable resource to insurance carriers, actuaries for up-to-date insurance premium modeling, or government agencies to assist with system-wide care delivery modeling and monitoring.

Figure 7:
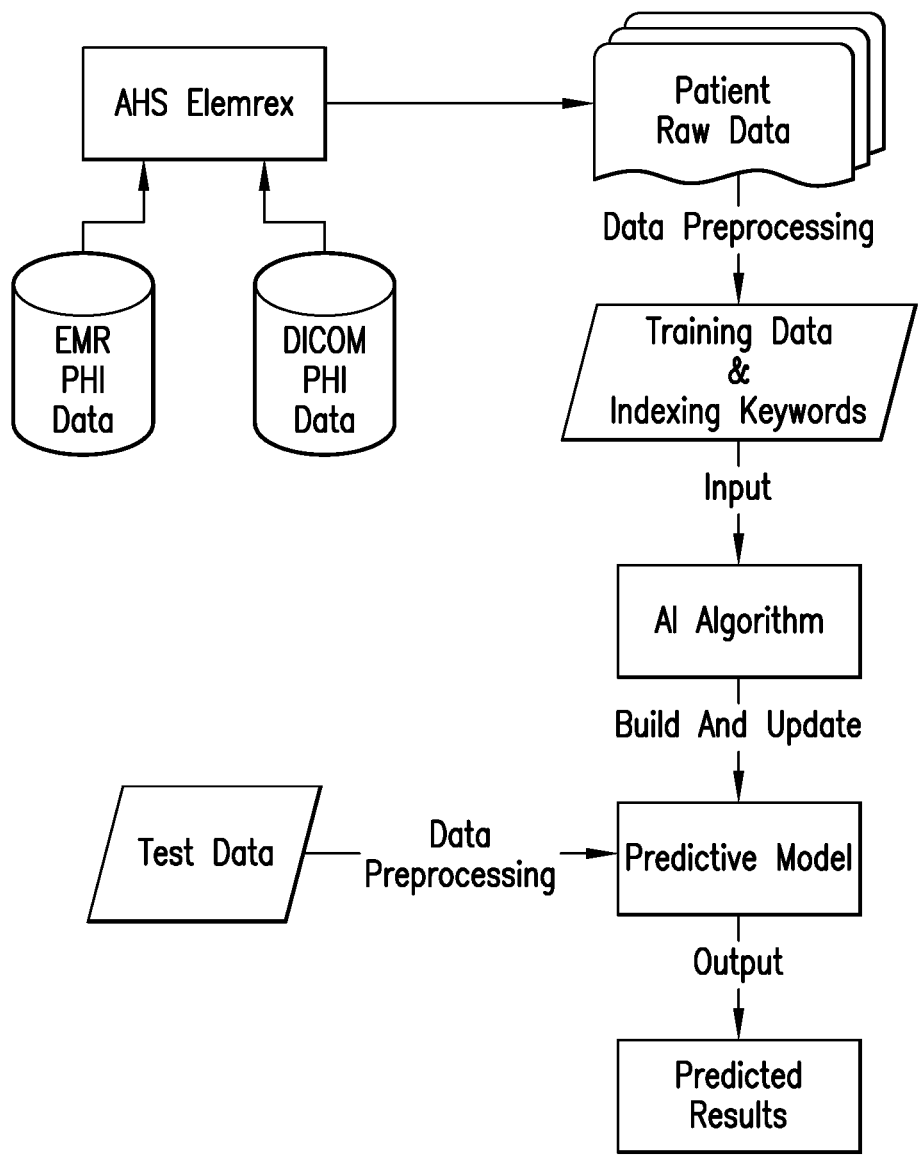
FIG. 7 illustrates a flowchart for adding new patient data to an existing grouped studies, in accordance with an embodiment of the invention.

FIG. 7 illustrates a flowchart of the construction of the how the AI enabled system will add the new patient data to the existing grouped studies for a specific collation of information and keep updating the results as new studies are being added every day. In the training phase, the raw patient data are processed to extract metadata and index the studies based on keywords. After which the system will build a predictive model using the AI algorithm with the training data available and it keeps improving by providing more patient data over time. And in the prediction phase, the patient data is inserted to the predictive model to display net effect on the outcome of the diagnosis, practice, referrals and treatments rendered.

The collating of information by digital imaging and commentary from physicians or interpreting physicians who create reports is exactly how the digital gathering of PHI and imaging studies is integrated with input physician experience and new information from a new patient to organically, exponentially grow the technology's big data pool, that is instantly categorized into clinically applicable subsets for immediate use. The above information is derivable from the physician transaction log and the physicians' input when they are pulling information the first time, and are able to replay it. The expansive application of the system storage methods enable the viewer to pull previous transactions and commentary, but can revert imaging studies back to their uncommented upon or marked up original format for fresh interpretation, add insight, and be able to share reviews with other colleagues that were historically pulled and accessed, or in real-time as colleagues can look at the technology transacted images and PHI together, just by signing into the system.

Master patient indices (MPI) are commonly discussed in the healthcare and EMR industry to address a technological challenge of patient and personal health information (PHI) matching accuracy and reliability. The present inventions system defines master patient index in the following way that defines its functioning as an integral part of the ELEMREV™ system's "Patient Provider Matrix (PPM)":
1. The MPI has standard categories of name, Social Security No. (when available), date of birth, gender, address, etc.
2. The differentiator in the system's MPI is that the patient's treating physicians validate identity with PHI with each organic engagement with the system when they affirm and validate that the patient name is matched with correct PHI/imaging studies, as physicians know the tests they order, the patient's clinical characteristics, the imaging study results they are seeking based on what they have ordered, so we are able to capture and integrate the physician knowledge of the patient as the new type and significantly reliable validating source. The system provides validation scores based on physician input as to match patient ID and information that is pulled and viewed.

The present invention's system MPI algorithm works by combining information from DICOM studies and PHI records. When data is obtained from DICOM modalities (PACS) or EMR systems heuristics based matching algorithm uses data from demographics (name, gender, age, location), problems (problem name, type), medications, allergies, and DICOM metadata (such as modality, institution, referring physician, and study description, Radiology reports), to perform patient matching. If successive records contain same values across different attributes, this will increase the chances of the records being tagged as belonging to the same patient.

In the first level of matching, the system looks for matches again using attributes such as social security number, first name, middle name, last name, gender, and date of birth. If a perfect match is obtained, the patient records from the EMR are linked to the "Patient Provider Matrix (PPM)" that assigns a master patient index number that uniquely identifies that patient. The system differentiates and logs an assigned master patient index number to each accessed source PACS or EMR system's medical record numbers for system AI learning to accelerate subsequent patient search and fetch features, as well as data matching. If a match doesn't occur, then they are marked as probable matches. For each record from the set of probable matches, the system will obtain historical clinical information of the respective patients to perform a second level of matching. This includes data such as medical problems, medications, and allergies grouped based on timestamp. The system checks for consistency across all the probable matches and obtains a consistency score. The systems' PPM algorithm works by combining information from PHI records and DICOM studies. When data is obtained from EHR systems and DICOM modalities, heuristics based matching algorithm uses data from demographics (name, gender, age, location), problems (problem name, type), medications, allergies, and DICOM metadata (such as modality, institution, referring physician, and study description), to perform patient matching. If successive records contain same values across different attributes, this will increase the chances of the records being tagged as belonging to the same patient. If the system still fails to match the records to a patient with full certainty, the system will mark those records to be looked at by physician users of the ELEMREV™ system, who will perform the match manually for a third level match.

Figure 8:
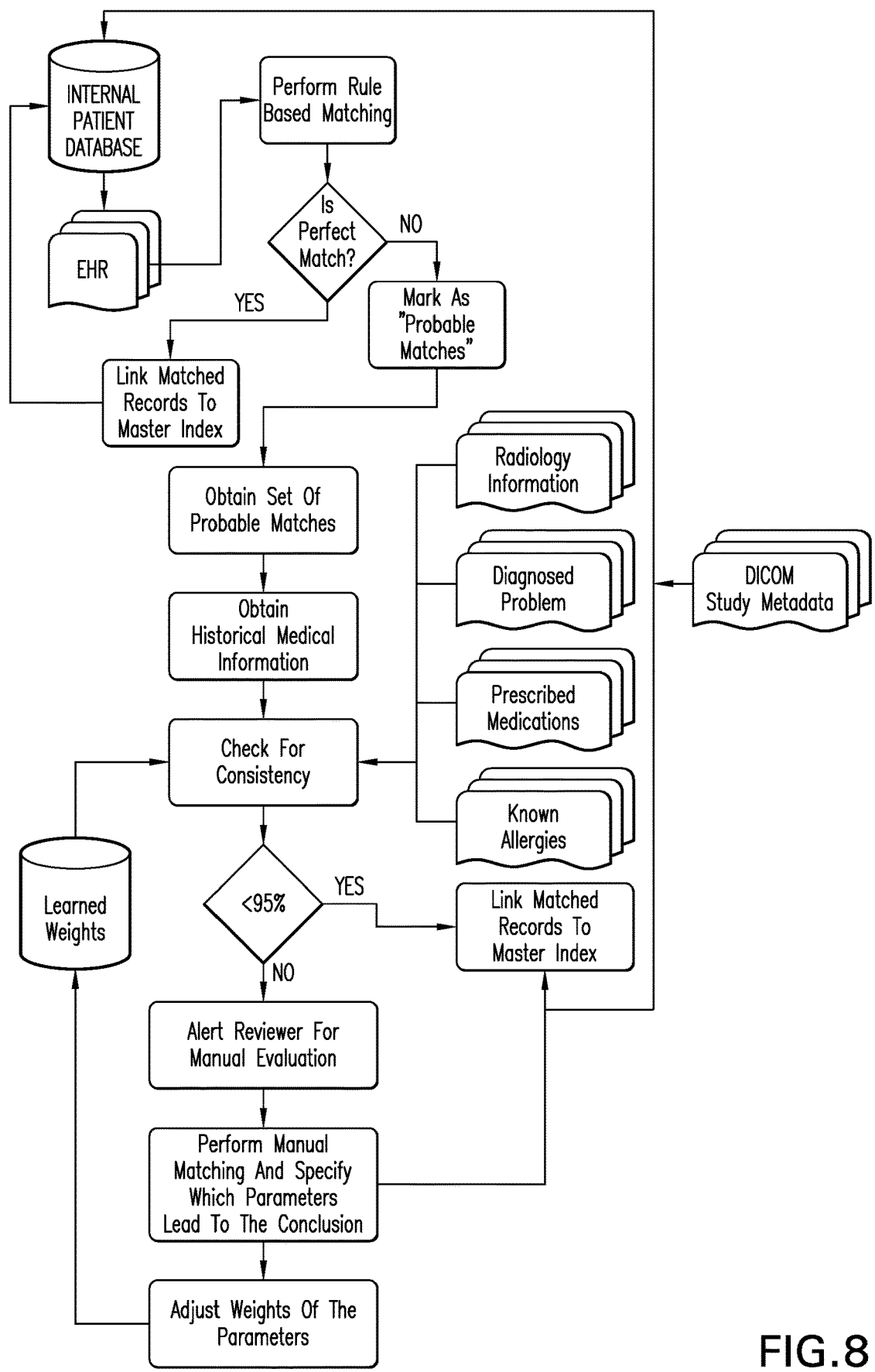
FIG. 8 illustrates a master index process, in accordance with an embodiment of the invention.

FIG. 8 illustrates the master index process. For example, the clinical information for a patient named "John Samuels" might indicate that at time T1, two head CT scans were performed for the patient at a radiology lab R1. At time T2, he was diagnosed with a problem P1 and prescribed medications M1 and M2. However, clinical information for a patient named "Johnathan Samuels" might indicate that at time T1, two head CT scans were performed for the patient at a radiology lab R1, and that he was diagnosed with problem P2 and prescribed the medication M3. Since the medical history for both the patients is <95% consistent, the reviewer is alerted and presented with the complete information so that they can manually evaluate if the records indicate the same patient. The reviewer also has to specify what parameters helped them arrive at their conclusion, such as patient clinical history familiarity, which will be used to update the weights used in checking for consistency. In this scenario, the problems diagnosed and medications prescribed for the two patients are different, and so these parameters will be selected by the reviewer.

As an example: If there are 10 PHI data pull entries in a patient's transaction log and the medication lists have varying numbers of medications in 3/10 entries, the confidence level of the patient's ID based on medication listings would only be 70%, to which the reviewer would be alerted if <95% consistency. This is where the unique concept of organic and artificial intelligence accumulated data validation comes into play as being IP patentable for the ELEMREV™ PPM and MPI validating system. With alerting of only a 70%, i.e., 70% validation rating if the patient's information matching based on medication listings alone, the system will request from the reviewing Doctor if he wishes to view and compare all lists and the AI opens all screenshot medication lists from the 10 log entries and enables the Doctor to review date and time stamping, open the problem list or allergy categories in any of the 10 logged problem list or allergy screen shots, analyze and put together a date sequential clinical work flow pattern that the reviewing Doctor can then evaluate and check one of two responses: 1) clinically consistent, or 2) clinically inconsistent and suspicious that displayed data may not be from the same patient. There will be a liability disclaimer for all evaluating reviewers. Statistical data from the number of reviewer responses is collated and displayed, as well, as a newly defined classification for reimbursable physician telemedicine engagement. This is just one category within one method of the PPM's Physician-patient information comparison that will create a validation score for a fourth level MPI patient identify validating. Another will include the transaction log for images that will use straight forward difference algorithms that can be easily validated, based on date, time, image type and location of imaging source as necessary parameters for comparison, as the fifth level of the physician assisted patient identifying protocols.

If 10 image pulling transactions are listed, and there are two pulled imaging studies performed on the same date that are separately listed, but took place in two different locations, that will be alerted for the reviewing Doctor to investigate. If 2 head CT scans were performed in 2 different states on the same date, then the reviewer checks the category of being clinically inconsistent and requires further investigation. Should there be imaging studies that are listed under a female patient's log named Jamie, that could be a female or male name, but the test is a testicular ultrasound imaging study, then the reviewer would check that there is suspicious clinical inconsistency and requires further validating. Level 5 validating allows any reviewer to look at statistical and commented inconsistencies and any statistical probability calculates that all logged information comes from the same patient's transacted data logs and the formatting of the statistical reporting, alerting and confidence evaluating that the PHI/images listed in the PPM for a patient all belong to that patient, and the way the system recruits Physician input as part of the validating process is dynamic and organic to patient data accessing activities with normal system use. The system reports the number of physicians to access and cast votes to build power of the data analysis.

Figure 9:
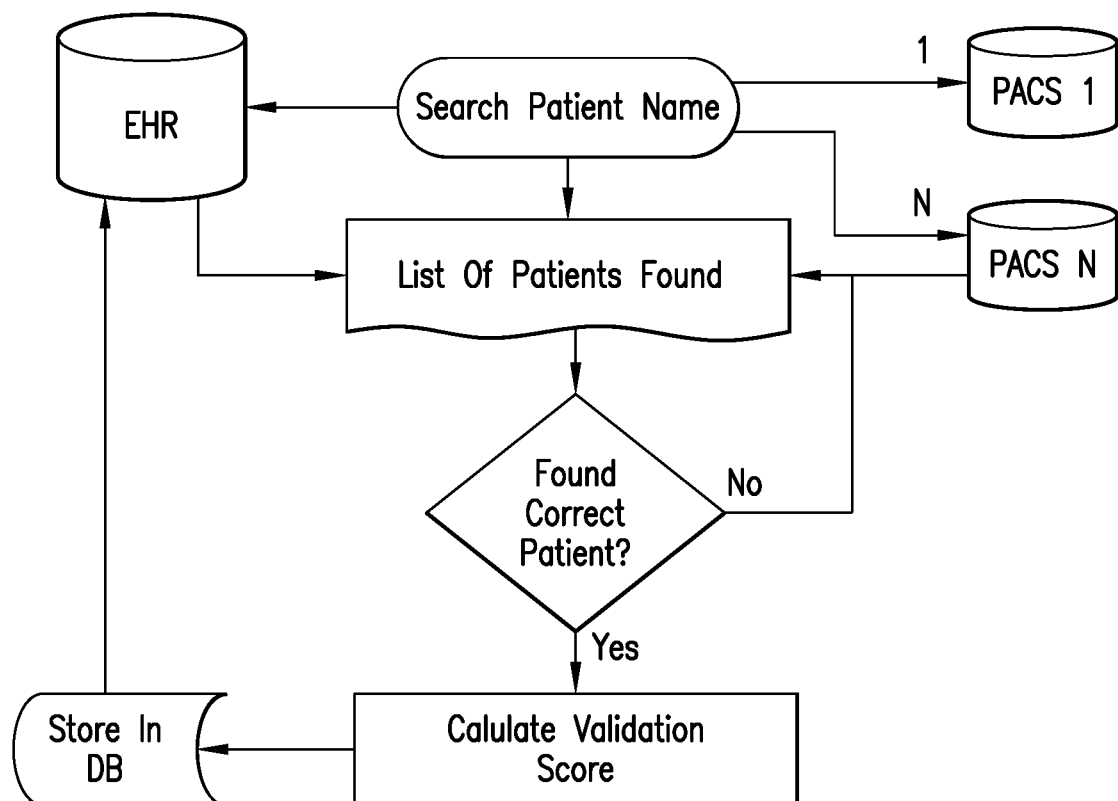
FIG. 9 illustrates a flowchart construction of how the right patient is determined by a physician when there are duplicate entries for a patient, in accordance with an embodiment of the invention.

FIG. 9 illustrates a flowchart construction of how the right patient is determined by a physician when there are duplicate entries for a patient. A physician searches using ELEMREV™ platform which fetches the data from multiple location along with locally stored information. Physician then selects one of the duplicates as the right patient upon which a validation score is assigned on the basis of how many physicians voted that the patient found was correct. And these results are stored in the system. Afterwards, when another physician pulls the same patient data, the system will display the validation scores against that patient based on the ranking by the physicians.

PPM Invention Feature Summary Includes:
- A) Level 1: Identify patients by their expanded identifiers, such as name, gender, DOB, SS #(if available), address.
- B) Level 2: Additional cross matching with specifically accessed PHI subcategories such as medications, problem lists and allergies to further refine identity confirmation as a unique digital approach.
- C) Levels 3-5: Organic confirmation by treating physician validation of a patient through matching PHI and DICOM image reviewing brings a uniquely validating integrated approach to the technology. By physicians viewing patient data checking confidence level when reviewing, such as i) confirming pulled data matches the patient name, ii) confirming specific ordered test results and matched clinical information coincide with recollected patient history, physician engagement is designed to enhance technological health data matching algorithms.
- D) The unique PPM technology security algorithm confirms accessing physician identification is to include instantaneous confirmation of NPI, active state licensure, and uses geolocating technology to identify and confirm position of a confirmed/PPM listed portable device. These are in addition to more typical physician entry dual confirmation UN/PW restrictions. The PPM technology is being designed to maximize patient privacy by restricting subscribing physician access to all patient PHI through cross referencing test ordering physician identification, physicians who have reviewed studies, such as Radiologists and Pathologists, names of physicians who have previously accessed a particular patient's PHI in the past, and to those restricted by patients through a mobile app. AI technology enables the system to expand and learn physician permitting algorithms for each accessed PHI file.
- E) Once any subscribing or guest physician accesses the PPM to pull a patient's PHI, the PPM creates a patient app home page that lists all accessing physicians, the physician identifiers used to confirm their identity (generically stating they required a dual confirmation UN/PW entry), and a listing of each and every patient data transaction that is viewed for patient transparency. Patients will be able to access all the names of accessing physicians and be able to add names of other doctors or facilities which get uploaded to the PPM as part of its AI that learns each patient's individualized prior treatment network. Patients can contribute at any time, including names of laboratories or other testing facilities.
- F) The PPM will analyze collected data for each patient, including:
   - physician accessing with identity confirmation algorithm data collected and used,
   - patient accessing dates, frequency,
   - patient identity confirmation and algorithm data points used for confirmation,
   - patient added provider names,
   - provider granted temporary access to consultants with time clock.

The present system creates the foundation for AI learning to match relationships between patents and providers and can internally generate further statistical AI based on patterns of physician and patient engagement, which is sellable to Insurance Carriers, patient organizations that are self-insured, etc.

- G) The second level of the PPM AI is founded within the functions already built within the transaction log (summarized elsewhere), which is the dynamic element of the PPM from which patterns of physician activity in reviewing patient data are learned and statistically analyzed to provide invaluable learning that quantitates and qualifies physician interactive activities, again of interest to insurance carriers, actuaries, malpractice carriers, etc. as a sellable item.
- H) Another patentable element is the organization protocol of the patient files within the PPM. For each patient with moved PHI, ELEMREV™ assigns a system identifier, matching listings of each unique identifying number within each PACS or EMR system from which patient data is accessed and moved into the system. The permanent matched listings facilitate targeting and repeated data fetching from a previously accessed PACS or PHI system to enhance speed of new data pulling or transaction replays as part of PPM AI learning.

Figure 10:
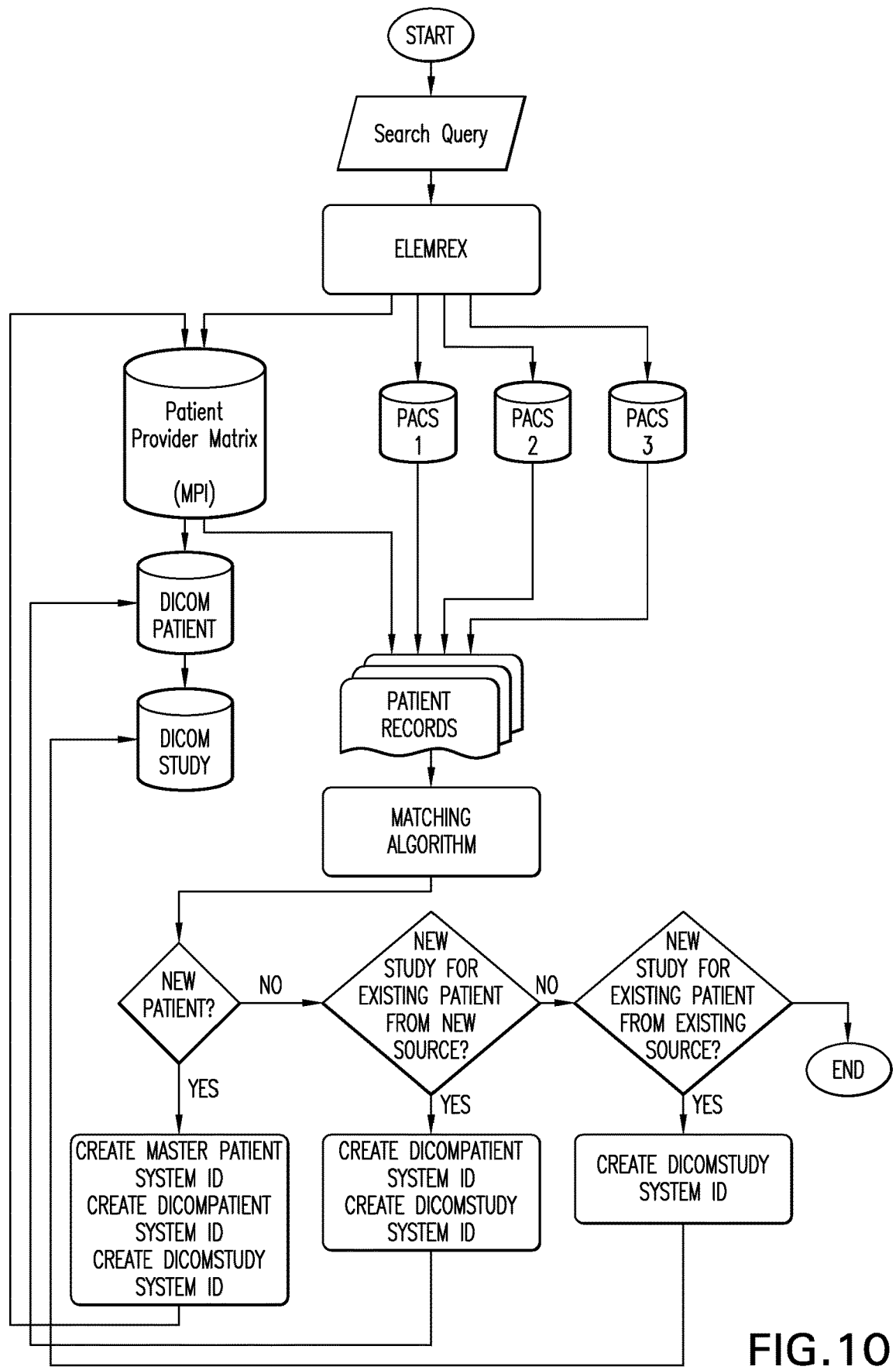
FIG. 10 illustrates an alternative embodiment of the search query, in accordance with an embodiment of the invention.

FIG. 10 illustrates the search query of the present invention. When a physician enters a search query, ELEMREX™ searches its Master Patient Index, and also all of the PACS servers that it's connected to, to find patient records matching the query. ELEMREX's matching algorithm determines if any of the records obtained from remote sources belong to a patient already existing in the system. In such a case, the studies after being retrieved are assigned with system identifiers that are linked to the Master Patient's record. But if the studies found belong to a new patient, i.e., a patient whose records are not present in the system, a new system identifier is created for the corresponding patient, and the studies after being retrieved are assigned with their own system identifiers, and linked to the newly created identifier for the patient.

- I) By keeping track of each physician's transactions, the PPM uses its AI to analyze practice data review patterns for each Physician subscriber that are internally available to each subscriber, but can be statistically summarized for big data sale to insurance companies or health profession researchers scrubbing Physician identity.
- J) The PPM will generate electronic health information interoperability statistics able to be identified, scrubbed, and sold.
- K) Subscribing physicians are provided with transaction logging as a service for validating their invoicing for telemedicine services able to be sold to insurance carriers that request transaction validation details for subscribing practitioners.
- L) e-Sign will allow patients to digitally fill in their Demographic data and sign AHS's HIPPA consent forms using a mobile device or a computer. Availability of digitally completed forms through our ELEMEREX™ portal provides Radiologists with immediate access to pertinent clinical data, allowing them to confirm patient identify and match Radiology imaging and reports entries to the correct patient within our system taking advantage of their clinical association as part of our innovative leveled matching protocols. All the patient data collected through e-Sign will be stored in a DB that will form the basis for building the ELEMREX™ PPM database.

The invention's e-Sign patient demographic and HIPAA permissibility provides PPM entry validation for Physicians that supersedes remote portal entry permissibility. Permissibility is ultimately the jurisdiction of patient's primarily, and permitted Physicians needing to consult others secondarily. Examples of the PPM design permissibility advantages include:

Female patients limiting ob./gyn history access to certain specialists,

STD data restriction to only treating specialists of no future historical value to most specialists, Any patient leaving a physician's practice will now have the ability to restrict that physician's future PHI accessing, in contrast to erasing potentially critical data that may prove to be vital in an emergency clinical situation or when possibly needed for comprehensive health record evaluating as part of, for example, cancer management.

Ability of patients to review and update their personalized PHI access granting physician lists through the PPM app.

Patient ability to view which physicians have reviewed their PHI and when.

Ability of the system to validate and emergently notify patient or designated advocate(s) through messaging requiring immediate response to an emergent request to unrestricted PHI accessing in cases of patient incapacity in an unknown emergency setting. Failed messaging response automatically releases emergent access to specified basic PHI that can be expanded by the patient or prior approved advocates through the app.

The security and permissibility algorithms integrated in e-Sign will enable AI to use continuous search and validation algorithms to verify and confirm identity of patients and providers. This invention design provides PPM updated matrix verification and statistical validation of patient AND physician identity with everyday use to continuously monitor, update and validate permissibility in the PPM.

An example would be there are 250 patients named Patrick Quinn in the database, and 20 John Williams in the physician database. For patients, level 1 identifiers of name, address social security number (if available), date of birth, gender, are used and able to differentiate all Patrick Quinn's. Patrick Quinn #66 moves to the same address as Patrick Quinn #22, as they are father and son, for example, where the younger must now live with the older because mom has died. There are no SS #'s for either in the system and they were born on the same date, but data entry error has the same birth year listed for both. They both see the same doctors and level 2 verification is of no assistance as both father and son are healthy, with no medications and no allergies. Physician validation (levels 3-5) is unhelpful in this case as the same doctor who now sees them both has yet to meet the son for the first time. Level 6 geolocation (see below) differentiation is of no value as the patients' common home address and inquiring physician locations raise no red flags. e-Sign will be able to differentiate at a seventh level of validation by pattern recognition technology identifying the difference in the two Patrick Quinns' signatures. e-Sign will notify patients when going for a new study>3 months apart in time of ordering that they need to update their signature, creating a library of signatures for each patient from which pattern recognition e-Sign software can differentiate, and use algorithmic pattern analytics to determine if a new signature is within acceptable likeness tolerance of those on file. If not, the patient will be prompted to sign again using either: 1) formal signature, or 2) quick signature writing styles. Both will be available within the database for comparison.

e-Sign documentation will serve as a signature catalog, quickly becoming an expansive reference that is sellable as a separate product for use, for example, at voting stations to compare onsite tablet or cellular phone touchscreen written e-signatures as another potential layer of identity validating from which statistics are easily derived, as opposed to matching of written signatures in voter registration logs, from which analytics require manual validation and data entry, both more error prone and sufficiently time consuming to effectively serve as a barrier to expanding statistical analytic capabilities.

e-Sign integration within the ELEIVIREX™ PPM serves as a multi-level identity validation protocol enabling the invention to serve as a remote ID validation technology for, as an example, Financial Institution online services that may choose to license.

e-Sign technology security will systematically contact patients with alerts to notify them of any forgeries being submitted at the time of a radiology or laboratory test being performed when and if someone else e-Signs rather than the correct patient to use their insurance coverage benefits that can infrequently occur, or with substance abuse testing. Physicians who elect this notification service will be alerted by text, e-mail or other forms of messaging to this event in addition to primary patient alerting.

As each patient enrolled in ELEMREX™ requires a minimum of 1, if not 2 registered advocates, patients will be able to input advocate demographic data into the system using e-Sign that will then push contact and require all advocates to register e-signatures. The patient advocate data and signatures stored in the patient PPM and will allow for rapid, reliable notification and system verification when emergency advocate permission for PHI sharing is requested under the circumstance of patient incapacity.

e-Sign level 7 identity verification will only be initiated by the system may all prior level identity confirmation and level 6 ELEMREX™ GPS location confirmation technology inadequately confirm patient or provider identity validation. An example would be reaching level 6 identity verification demonstrating an emergency PHI release request is coming from a cellular tower in Bejing, with level 6 geolocation validation denying information release before the system would require patient or advocate e-signature confirmation.

L) BlockChain technology integration will serve as the foundation for audit-ability of patient data accessing. Blockchain can be used by different components including e-sign, PPM module, PACS-DICOM gateway and User-search/View module to store the access requests, which can then be later (offline) analyzed. Blockchain can also be used to store the permissions themselves and be used for cross-referencing before allowing access to patient data. Such access logging and permissions can be available in a transparent way to patients, healthcare professionals, and system administrators.

BlockChain permanent accounting of all permission and transaction interactions will be logged as part of the PPM matrix design that will be replicated on Blockchain. Selecting BlockChain open, semi-open, or closed architecture will be left open and predicated on maximizing patient PHI and permissibility granting confidentiality and security.

Where Blockchain invention technology will be of higher specificity and security is with cross-checking between e-Sign and PPM matrix data with each and every BlockChain keyed entry to use AI to determine: 1) Blockchain can be used to cross-validate and be used as a source of information to notify patients if there is information access being requested or assigned where ELEMREV™ authentication is statistically questioned that patients can choose to override or verify with an alert response notification; then 2) if there is no patient response and the inquiring physician questioning scenario is unresolved, the patient is provided with push notification along with demographics of the requesting physician, such as name, specialty, location, and contact information to be able to reach out and communicate with the provider directly to validate authenticity, providing the patient with real-time knowledge regarding key granting and PHI accessing, may the patient select this feature.

Functional time limits associated with each access log or permission can be stored on Blockchain too which can serve as cornerstone entries to be utilized for restricting and directing physician permitted accessing to PHI. The invention focuses on unique key coding that will also coincide with Physician-specific HIPAA release time restrictions, creating key features and functions within the Blockchain that are able to now be physician-specific. Not all keys will be the same, with key design incorporating patient controlled PHI physician limiting accessibility, that again can only be overridden in an emergency request for full data accessing, as might occur during the unknown unconscious patient scenario. This type of Blockchain key accessing authentication and permanent accountability process enables the ELEMREV™ invention to solve for HHS mandated HealthIT changes requiring patients to now oversee and manage their personal electronic medical records.

Licensing of Blockchain PPM permissibility technology becomes an opportunity for patient participation in health information accessing and accountability to become universal across the electronic health information spectrum, much like hybrid automotive technology is licensed from the Toyota Manufacturing Corporation by hybrid vehicle manufacturers.

Pharmaceutical Industry: The current invention contains features that will enable ELEMREV™ to remotely identify patient records which match certain clinical and demographic criterion within EMR systems to streamline pharmaceutical clinical trial patient recruitment, while providing capability to monitor patient journeys in real time for AI and Researcher comparative analyses. For example, a Pharma Company might be looking for patients of certain age, race and clinical problem who have been treated with a certain medication in the past in order to identify subjects for a new test. This process today is a very costly and ad-hoc process primarily because data is segregated and there is no advanced way to look up patients from diverse systems utilizing complex Boolean queries.

The present system performs a reverse indexing of patients EMR-MRN i.e., stores a key value store with Patient Id based on Problem, Allergy, Medication and Dates. e.g., "asthma: emr+mrn-id" Subsequently, the system applies complex algebra on this data set utilizing queries involving an exact string match or similar string based on a specified dictionary. Because a reverse index is maintained, patient info can be looked up using patient EMR-MRN and further, results can be filtered or an 'AND' query can find patients with, for example, diabetes and a particular medication.

The PPM invention design not only enables remote clinical trial patient mining from EMR servers, but then provides real-time remote accessing of patient journey clinical data through automated search and fetch protocols. These will provide Pharma Researchers with identity blocked patient scheduled prescription and testing compliance, automate notifications with test results that fall outside of set parameters, analyze, stratify and organize participating patient data points beyond required monitoring criteria using AI analytics and stratification to identify unsuspected variations in medication interactions, determine side effect etiology, multivariable data point correlating, and provide real-time ongoing patient treatment response and alerts to maximize participating patient safety.

The system can be further advanced by annotating clinical test outcomes with patient segments on which the query was run, leading to creation of an advanced decision tree and an advanced feedback system to the researcher in Pharma Companies. In other words, experimental outcomes can be used to annotate patient Info leading to smarter queries and segmentations/analytics because of a richer data set being created.

The present invention also teaches a "Medical Organic Digital Library" (MODL) that captures its unique functional elements and built in interdependence between collected, collated data and the essential, integral organic physician interaction that is critical to provide clinical interpretation and meaning to that data.

In another embodiment of the present invention, the creation of the MODL health information exchange system that, through its use, organically builds the world's first physician/patient data learning environment that will transform health information into a clinical library of current, real time data that is accessible and directly applicable to aid Physicians in their clinical practice. The creation and organization of big data, with routine daily use, allows for the present invention's system to stratify, classify, statistically analyze and present in a way that collates commonalities for Physicians to access and base current treatment decision making for like patient cases they are currently dealing with in the present. This fundamentally reestablishes the paradigms of scientific methodical gathering, analyzing, and collating of information after management has been rendered, the inherent antiquated nature of such gathered and organized information, and brings routine daily technology use into play as information is routinely analyzed and integrated when it is gathered for timely application in real-time patient care rendering by Physicians.

Figure 11:
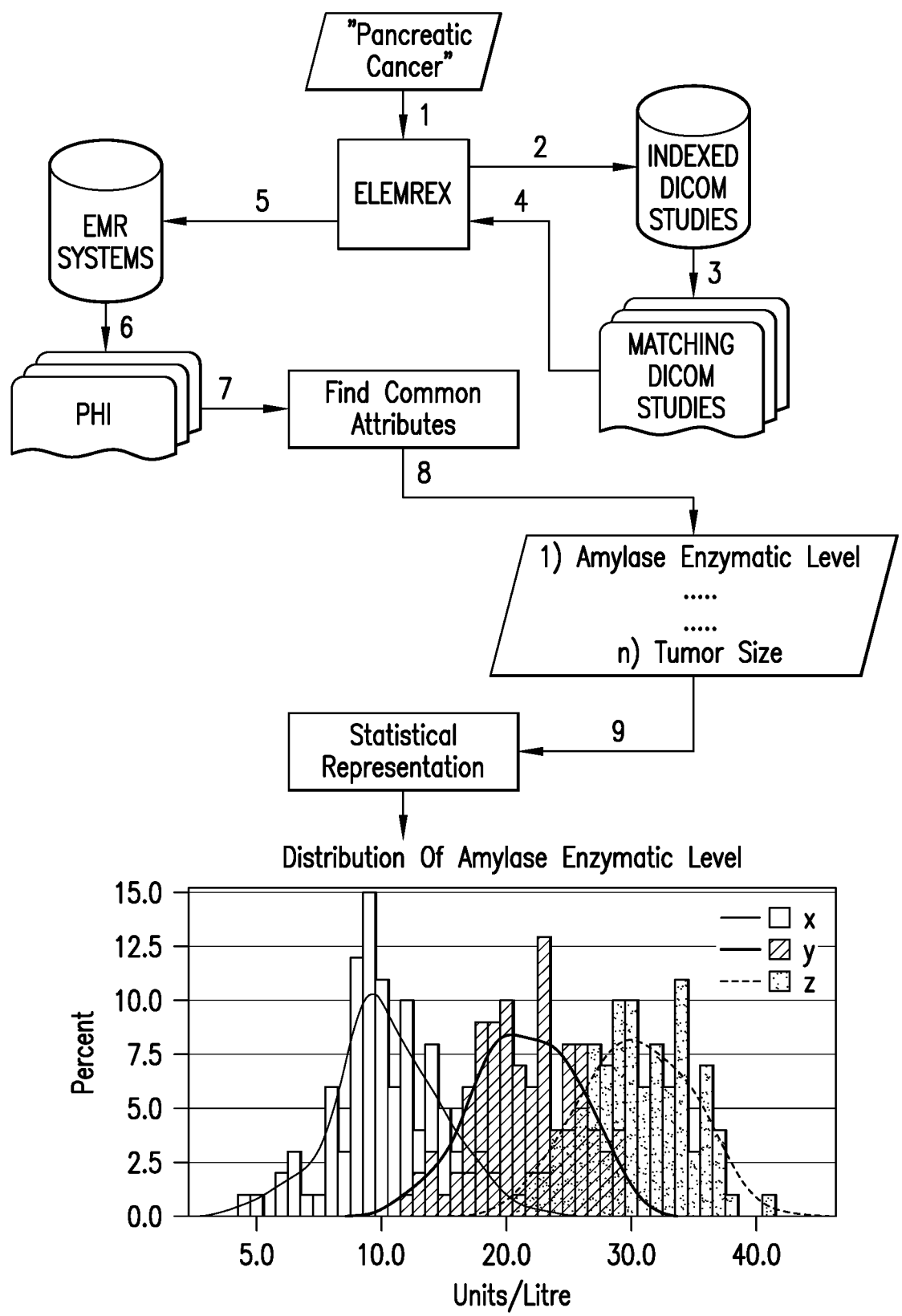
FIG. 11 illustrates an alternative search query, in accordance with an embodiment of the invention.

FIG. 11 illustrates an embodiment of the present invention. A physician enters the search query "Pancreatic Cancer". ELEMREV™ searches through all of the indexed DICOM studies to find the ones that are associated with the tag "Pancreatic Cancer" as entered by the user. Using metadata from the studies, ELEIVIREX™ queries multiple EMR systems to retrieve consolidated Patient Health Information of the patients whose studies were returned. Using the PHI records, ELEMREV™ finds out the attributes that are common to all the records (such as "Amylase Enzymatic Level", "Tumor Size", etc.) and uses those attributes to generate descriptive and inferential statistics.

According to an embodiment, the invention's MODL technology is intended to shift the paradigm of routine physician 'asking' for outside guidance or assistance away from the currently perceived 'weakness' or practice 'insecurity' toward routine physician MODL database accessing as an interactive tool physicians can utilize for real time clinical researching as part of their daily practice.

Figure 12:
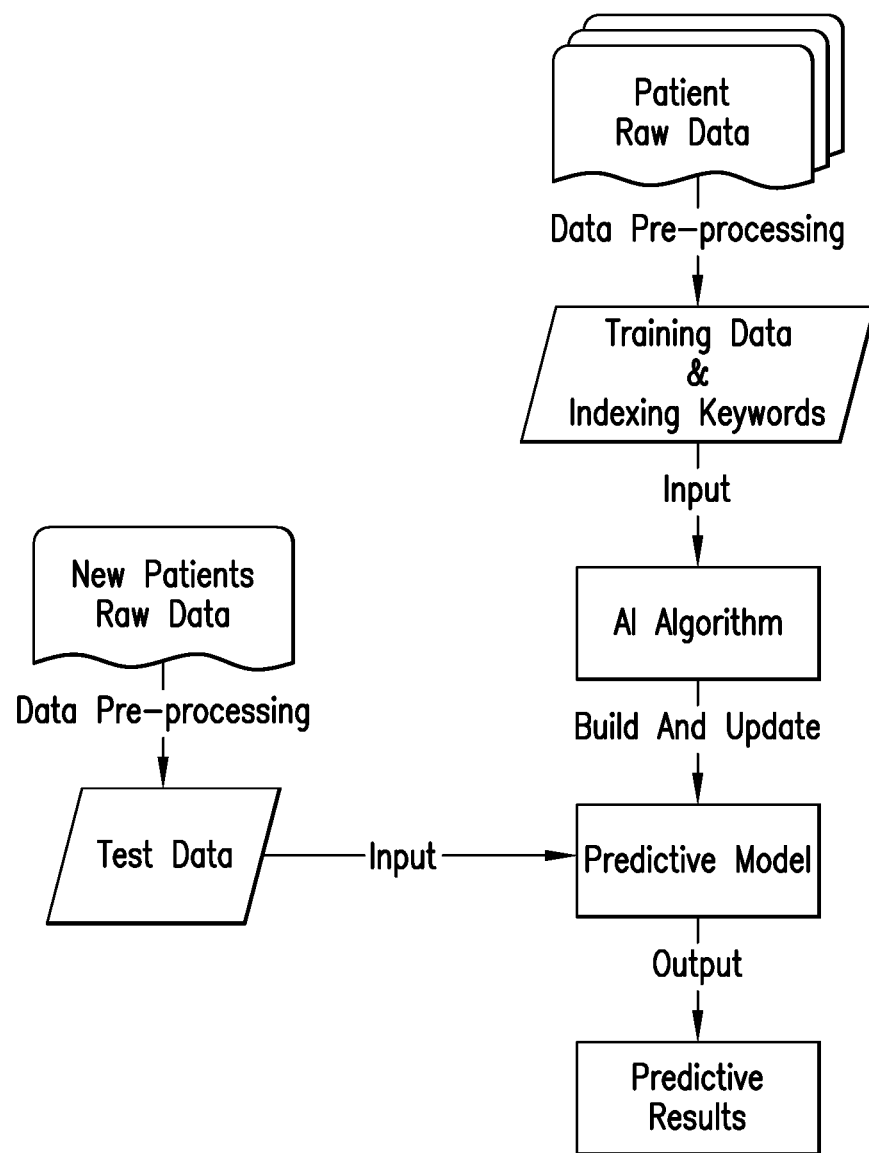
FIG. 12 illustrates an alternative embodiment of a flowchart to add new patient data, in accordance with an embodiment of the invention.

FIG. 12 illustrates an alternative embodiment of a flowchart of how the AI enabled system will add the new patient data to the existing grouped studies for a specific collation of information and keep updating the results as new studies are being added every day. In the training phase the raw patient data are processed to extract metadata and index the studies based on keywords. After which, the system will build a predictive model using the AI algorithm with the training data available and it keeps improving by providing more patient data over time. And in the prediction phase, patient data is inserted into the predictive model to display net effect on the outcome of the diagnosis, practice, referrals and treatments rendered. The collating of information by digital imaging and commentary from physicians or interpreting physicians who create reports is exactly how the digital gathering of PHI and imaging studies is integrated with organically input physician experience and new information from a new patient to organically, exponentially grow the technology's big data pool, that is instantly categorized into clinically applicable subsets for immediate use. The above is derivable from the physician transaction log and their input when they pull information the first time, and are able to replay it. The expansive application of the system storage methods enable the viewer to pull previous transactions and commentary, but can revert imaging studies back to their uncommented upon or unmarked original format for fresh interpretation, add insight, and be able to share reviews with other colleagues that were historically pulled and accessed, or in real-time as colleagues can look at the technology transacted images and PHI together using the 'Virtual Bedside" collaborating feature just by signing into the system.

A differentiator of the present system's format is that real-time communicating and collaborating by a group of physicians is logged, so that final comments and/or conclusions are being entered not just by one physician with bias, but by team physician evaluating, assessing and concluding that adds another dimension to the interpretation commentary that is the next generation above what singular physician input can provide. Further organic physician involvement includes reviewing of information that has been analyzed and statistically reported, and receives validation scoring by data reviewing physicians, such as affirming, questionable, unlikely subcategories that are statistically collated for physician support of patterns that the system gathers, organizes and creates. Much like voting, the system will integrate the physician experience into the information validating methodology, as well as identifying physician type to identify and stratify voting based on subspecialty. Example: A Dermatologist commenting on Pancreatic Cancer would be less weighted by the system in comparison to that of a Surgical GI Oncologist.

The present invention's system maintains a master table (FIG. 13) that consists of unique keywords, or tags. The text from annotations created by physicians on DICOM studies, along with other DICOM metadata, is used to infer keywords that describe the imaging study. These keywords are used to create a relationship between the DICOM studies, and tags from master table ('global tags'). In the Search By Tag user interface, the search term entered by the user is passed to the REST API that runs in the backend, which in turn calls the globalTagService in order to retrieve the DICOM studies based on the tag entered (getStudiesByTag method). This returns a list of studies that have been mapped to the search term entered.

When a physician opens a DICOM imaging study in the viewer, a websocket session is created between the system's application and Ambra's servers. This active session is used to capture annotations and their metadata created by the physician, and is retrieved and stored in the system. The raw text from the annotations data is processed to identify important keywords and tags that can be used to describe the DICOM imaging study. Mappings are created between the study and the identified tags, and this mapping information is stored separately. When a physician initiates a search, the keyword is looked up within the systems mapping tables, and a list of identifiers of DICOM imaging studies mapped to the entered keyword are returned. These studies are displayed on the systems user interface along with the relevant metadata. The official Radiology report that is routinely provided along with any DICOM file of an image can also be utilized to extract words or phrases the system is identifying as tags for the record.

Figure 14:
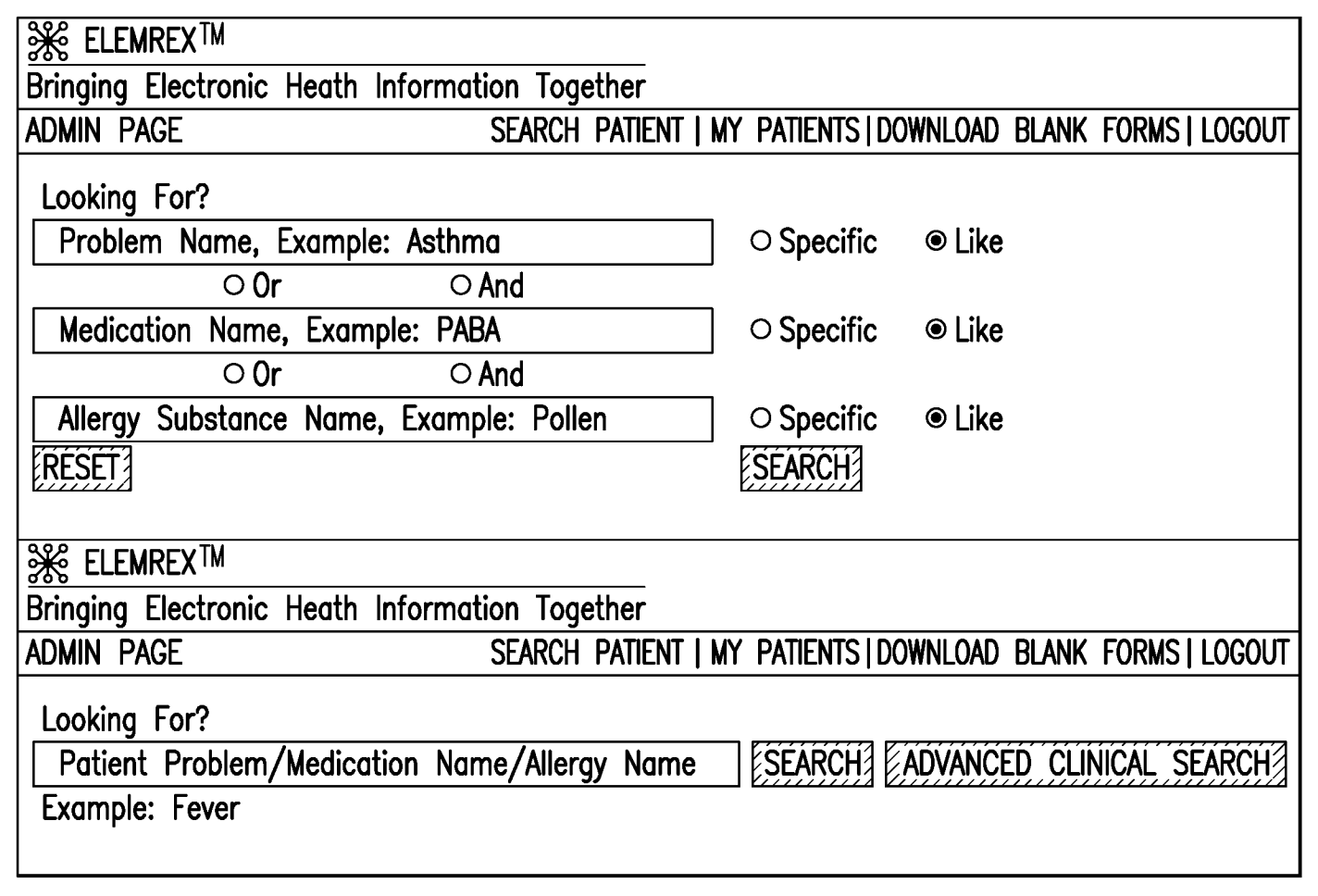

FIG. 14 illustrates a clinical record and image service screenshot of the present invention. In alternative embedment of the present invention, clinical records and DICOM studies are indexed, cataloged and clustered using keywords and tags for multiplicity of reasons including education purposes, comparison and analytics. Comments from multiple doctors on similar images or similar problems can be accessed leading to crowd intelligence being utilized for improving treatment outcomes. One way of identifying these tags would be doctors comments e.g., imaging comments and notes. Such notes and comments can be extracted utilizing text matching, regular expression or Natural Language Processing algorithms. Each image can have 1 or multiple tags leading to creation of a database with each tag having multiple images related to it. For example, "brain tumor" can have 100's of images, including both primary and metastatic lesion images within the database. AI integrating of physician input and analytic cohorts will assist in determining and expand statistically nuanced differentiators between the two brain lesion types as part of the invention's AI learning. Clinical advantage comes from isolated brain tumors that may be radiographically indistinct now being better understood based on nuanced AI cohort data to indicate clinical need for an unknown metastatic primary discovery, and reduce the need for high risk brain tissue sampling as the current differentiator between primary and metastatic lesions in uncertain clinical cases. Such a database of imaging studies can be utilized to study, teach and derive treatment knowledge.

ELEMREX's cloud-transferred data is transformed by routine physician review and commentary that MODL captures, analyzes, interprets, with subscribing and guest accessing physicians providing invaluable input to help stratify reviewed PHI in terms of relevance and importance, providing input as a foundation for transformative AI learning that is based on the doctor's clinical knowledge about particular patients.

This type of physician inputting into the MODL automatically takes place with every day, with routine ELEMREX™ use. In this way the technology captures physician interpretation and commentary to transform gathered patient data into a hierarchal organization that provides clinical relevance, interpretation and meaning for the next doctor who can access the same patent identifier neutralized library file based on catch phrase or word identifiers. When the next viewing physician adds his or her own interpretation or commentary, MODL's AI grows from organic interpretation by this next physician that then adds power to the digital statistical analysis of the technological platform it then performs.

As numbers and commentary regarding these types of case files exponentially grow, a vast library of physician knowledge, interpretation, clinical judgment and expertise is added integrated into the data files from which the MODL, through pattern interpretation, statistical analyzing and displays, amasses the clinical expertise of any number of reviewing physicians that: i) alerts the treating doctor of a newly input interpretation or commentary being added to his patient's clinical case file, AND ii) amasses a knowledge driven database any subscribing or guest physician treating a new patient can access for real time, up to date clinical knowledge based on system identified similar cases.

An example would be a subscribing or guest ER physician seeing a patient with an unusual set of clinical symptoms, such as nausea, diarrhea, rash, fever and high liver enzymes who then accesses ELEMREX™ and inquires MODL to identify any cases within the past 90-day period with identical symptoms and details of their management. The MODL identifies a list of stratified patient symptoms that match, then provides statistical analytics such as:

- 100% of patients underwent abdominal CT scans.
- 90% of the Radiology readings reported diagnosis of X.
- MODL identified words or catch phrases of Y and Z with recommended medicinal treatment with medication A.
- 90% of the CT scans identified this particular additional finding.
- 30% of the CT scans identified this particular additional finding.
- Which additional imaging studies were performed as an outpatient on dates following the initial abdominal CT scan?
- The ER physician can bring up the CT scan images of similar patients that have been patient identifier scrubbed.
- As the third phase of MODL AI development, the ER physician can access transaction logs for identifier neutralized patients who underwent the CT scans, which are stratified by the system that conducts statistical analytics, on demand, to identify which associated lab tests were ordered, test results, etc.
- Armed access to the MODL's comparable patient information, the ER physician has real time statistical evidence from which to make current treatment decisions for a patient with the unclear clinical presentation to streamline care he delivers.

To build a common patient foundation for MODL, a vast array of digital medical images nearly every practicing physician orders for the vast majority of all treated patients nationwide provides the initial, rich data source extracted from crawled accompanying Radiology reports. The MODL technology then transforms 2 dimensional images into what we are identifying as $4^{th}$ dimensional medical indexes, as physician input can take place regardless of location (3rd dimension) to add invaluable interpretations and contribute at any time ($4^{th}$ dimension), creating the ultimate organic/digital model for clinical team management that will optimize patient care using digital AI learning that does not exist today.

The present invention's system enables this invaluable organic/digital interfacing to take place among a group of participating physicians at once, in real time, allowing them to simultaneously review the same imaging study simultaneously, comment, mark, and interpret as a group, that is captured and archived by the system and able to be replayed at any future time by the participants, or open reviewing by another viewing physician who enters the library once patient identity has been scrubbed. The newly accessing and reviewing additional physician can then add input and commentary, contributing to the expanding AI for that patient within MODL.

MODL technology takes full advantage of the knowledge and experience of the entire physician community to transform simply gathered patient clinical data and the new $4^{th}$ dimensional clinical record that is immediately accessible to treating clinicians and shareable with the medical community, on demand. This technological advancement will make published clinical studies and case reports obsolete, which in and of itself is transformative. Patterns of clinical data interpretation, commentary and their digital management and statistical reporting will take place automatically within MODL, provide statistical and clinical evidence accessing in real time, and potentially supplant the need for dated publications.

Defining a 'rosetta stone' for the human genetic code: According to an embodiment, the MODL invention design will help write the dictionary correlates to the genetic code.

As part of the invention, the MODL will integrate a person's DNA mapping that is voluntarily available, now more popular than ever, with patient permission as a genetic footprint that becomes part of the PPM. Benefits include: 1) ultimate, most specific patient identifying characteristics being qualified and prioritized by integrated physician input, 2) providing a genetic integrating function in a secure HealthIT aggregating software platform of data from various genomic sources for patients with AI variation analytics creating a statistically validated, integrated patient genetic footprint.

Genetic mapping is at the very beginnings of mathematical combination and probability analytics in linking phenotypic genetic expression of normal human traits, let alone unlocking coded risk profiles for pathophysiologic or anatomical abnormalities and combinations, thereof, that underlie and place patients at risk for many medical conditions. MODL AI is designed to be able to learn statistical matching of phenotypic patient clinical variables with a genetic footprint, with physician input being critical to prioritize, confirm and mentally analyze and provide hierarchy of importance through MODL's organic/digital interfacing innovation. An example would be in patients with Basal Cell Nevus Syndrome, where genetically these people frequently form basal cell carcinomas of the skin surfaces exposed to the sun. There is an underlying genetic abnormality common to these patients, the syndrome has a spectrum of symptom and sign variations, that are likely associated with variations in the genetic anomaly yet to be discovered or phenotypically matched. Variations are more than likely distributed in a bell shape curve with other genetic and environmental factors playing roles, such that patients whom are fair with blond hair are at higher risk for greater phenotypical penetrance, i.e., get more skin cancers than say a person with darker, more protected skin and dark hair in a different geographical region. A physician validation request could easily enter important information, such as answer to a simple question as to whether a patient emigrated to a region or is native, modifying weight given to regional statistics.

The combined discovery potential of clinical input, phenotype matching and genetic variation statistical mapping offer AI input advantages to decode the nuances and mysteries of the expression of genetic variation combinations, once again, with the MODL invention's designed use that will exponentially advance utilization of genetic data and contribute to writing the dictionary as to genetic variation meaning for broader use.

By adding genomic mapping to patient's DICOM study, PHI integrated PPM databases within ELEIVIREX™, MODL AI algorithmic clinical data stratification will begin creating phenotypic mapping to the particular set of coded genes to begin creating a 'rosetta stone' of genetic language that we can expand our discovery as underpinnings of many patient clinical conditions. ELEMREV™ is designed to be able to communicate patient identifier neutral MODL machine learning to notify treating physicians regarding updates to their patient's clinical profile in the system, to educate the treating physician in real time when AI identifies and alerts of statistically significant analytical results, or when physician comment to a patient's identifier neutralized profile is made available and the treating physician elects this feature.

During routine daily system use, the current invention's AI statistical stratifying and matching will be able to create probability presentations, such as distribution bell shaped curves, pie charts, bar charts, x/y/z scattered data point mapping to create patterns that, with physician review and input, can provide an educational foundation for inquiring subscribers with which to evaluate patients currently being treated. As an example, a Physician signs in to the MODL and enters a set of atypical symptoms. In addition to clinically correlated statistical information regarding testing, treatment, treatment outcome, etc. as previously described, the combination of symptoms may statistically collate with an 85% rate of abnormal gene 35 on chromosome 13's locus, where the base pair in this high percentage of patients is reversed compared to the patient denominator in the system's database. Were this clinical presentation to be consistent with a pancreatic mass diagnosed in 75% of patients who undergo abdominal CT scans, not only does the physician become highly aware of correlated diagnostic and treatment modalities, but can have immediate impact on the physician's ability to more accurately focus care by directing the patient to oncological genetic research clinicians with the proper protocols at, say Memorial Sloan Kettering's clinic for pancreatic cancer management where this newly statistically isolated locus of genetic abnormality is brought to clinical researcher attention, and an investigating arm of research into immunopharmacological boutique designing options can be considered, or open a new product development research line for Pharmaceutical Companies to consider for pancreatic CA treatment, all based on MODL's correlating AI learning.

MODL can provide statistics and power analyses to help researchers and Pharmaceutical Companies prioritize activities that becomes a separately sellable product, in addition to providing a working method and execution plan for AI driven patient management tool for physician assisting. Until now, the unanswered question is: "What are the genetic predispositions for patients with pancreatic CA?". With the invention's particular MODL AI statistical and stratifying derivative capabilities, one answer becomes clinically recognized and statistically supported to modify treatment for that class of patients, specifically, available in real time, when timely effective treatment is so critically needed in this era when again boutique immunochemotherapeutic alternatives are just being discovered and introduced for individual clinical use. MODL will directly assist Pharmaceutical Companies and Clinical Researches statistically determine which immunochemotherapeutic development arms to pursue that can be of most value to the greatest number of clinically difficult, but identical patient groups with a common genetic anomaly.

With day-to-day MODL data collecting and AI learning, daily physician system use will contribute to discovery of the nuances within genetically mapped combination to phenotypic expression, in which there is an enormous knowledge gap. Physician input helps stratify clinical importance as to which phenotypic expressions require real life prioritizing based on patient impact, helping MODL focus and statistically prioritize AI learning underlying genetic normal and abnormal combinations. The invention focus is to conduct statistical and stratification AI activities for every patient once a data file is first established rather than addressing data analytics from a macro approach. In this way, MODL is designed to avoid the inherent big data analytical questions as to "where do we even begin looking and what questions do we ask?". MODL AI is designed from the beginning to utilize a micro to macro methodology to provide answer data sets to clinical questions before they may even be proposed by the engaging physician, who can then stratify level of importance to focus MODL's learning based on clinical relevance.

Advantages of the current MODL invention incorporating physician verification and interaction enables physician clinical acumen to recognize common traits between ID scrubbed MODL clinical profiles and those of their own patients. MODL recommended physician engagement within the "Virtual Bedside" protocols can, for this example, expand the pool of expert consultants to genomic, psychiatric and pharmacological experts to instantly create a multispecialty expert group of consultants that can assist in expeditiously treating a difficult patient's condition(s), saving both time and expense with enhanced expert care directing.

Normal and abnormal AI learning of genetic matching between genotype and phenotype offers another sellable product to not only Pharmaceutical Companies, but genetic testing laboratories and publishers as MODL use will expand a genetic/clinical correlate dictionary for both normal and abnormal pathophysiologic conditions. Today's curiosity of Ancestry.com and 23andMe genetic mapping for consumers, once input into the current invention, holds the key to understanding the 'rosetta stone' of genetic mapping and human species.

Physician engagement with MODL can also help stratify clinical conditions of importance by seeking data sets that are common, recognized by AI frequency of inquiry, that contributes to prioritizing likelihoods of activity to help filter management recommendations, incorporating abnormal genetic commonalities as an AI discovered patient stratifying filter that is presently unavailable. An example would be if there are 25 treatment options or protocols statistically analyzed and presented to a physician through the MODL for managing a group of symptoms, protocol prioritizing for the next physician inquiry through AI is updated based on what is actually ordered as treatment the inquiring physician initiates and becomes stratified data within the patient's PHI that creates machine learning to prioritize treatment hierarchy among the 25 treatments recommendations once the practical implementation of each additional patient's management is added to the electronic data pool. Integration of stratified AI genetic anomalies within the treated patient group's profiles enables MODL to provide statistical data that quantifies and statistically stratifies treatment outcomes for specific genetic abnormalities as a direct correlate. ELEMREX™ AI matches both normal and abnormal stratified chromosomal data enabling the MODL invention to collate with laboratory, digital imaging testing, clinical data, physician fund of knowledge, and create a chromosomal matching matrix that is able to be translated into intervention pathways, when identified.

Once treatment protocols are established and stratified by age group, MODL AI then provides an invaluable resource for age related genetic behavior abnormalities in children that can be investigated by AI recommended protocols and, based upon findings and clinical input from the physician, MODL will be able to correlate with other similar presentations and findings among the greater population and suggest genetic mapping and counseling to scientifically enhance early child intervention and family counseling. A real world example is for a MODL AI empowered validated statement an education counselor may be able to say to a parent: "With your child's particular type of autism, based on his genetic and clinical information, 98% of all children go on to lead normal lives without having to remove the child from the public school system as the current specialized curriculum offerings for children like yours has been shown to be effective". This correlates with potential stratification, treatment recommendations for various forms of autism in young children, while AI learning helps streamline while limiting unnecessary testing and can validate how these children are clinically managed. The MODL invention through daily use is designed to use AI algorithm to not only better write the genetic mapping to clinical value dictionary, but also the thesaurus as similarities will be identified in phenotypic with varying genetic combinations to begin to better understand and predict clinical spectrums that can narrow and focus care from core genetic identity to streamline clinical treatment as a new method for system-wide cost saving organizing.

How and why Physicians will initially choose to participate in contributing to this process begins with routine, more convenient accessing of their ordered digital images that are moved into and viewed through the ELEIVIREX™ technology. Sharing commentary with colleagues also treating a particular patient begins the creation of the MODL with routine system use and facilitates communicating capabilities about patient care among test ordering and other treating doctors. MODL automatically scans for common words or phrases within the written comments physicians enter to communicate with one another to accelerate and facilitate Team Management, much if it already taking place through texting and e-mailing, telephone conversing, as well as faxing of information today with integration being limited and often inaccessible. Automated MODL building and learning commenced with routine physician use of the system provides much needed integrating capabilities, serving to directly assist physicians when treating their patients and improve work flow.

As more accessing and commentary is added to a patient data file, with patient identifier scrubbing, doctors benefit from the added experience and expertise of others whom they otherwise would not know, potentially located in unfamiliar places. Today the reach and breadth of physician accessibility for Team Management oriented patient care is geographically limited and limited by familiarity of the primarily treating doctor. The technology design takes the advantages of physician team patient management by digitizing, not replacing currently used practices, and to expand physician input and participation.

Physicians can reference to find similar data about any patient they are treating that is not in a standardized report or paper, but is derived from real world physician experience and any number of patient experiences from around the nation, or world, through one digital source. Physician experience and expertise is added in an unsolicited manner and collected through commentary and transactional behaviors to build digital expansion of like imaging data base classifications that incorporate the organic input and commentary of members throughout the entire medical profession to create the first of its kind expert or experience based annotated medical imaging digital library "MODL". The library can be utilized for clinical treatment protocol outcome analysis, reference libraries for publications as a primary information resource, and even by patients with a medical problem who want to access and learn more about others with their condition and what many doctors have commented about it, providing patients with interactive access to system confirmed and stratified expert opinion.

The present invention's system provides an algorithmic search engine that can suggest search terms in order to aid the physician in obtaining refined patient results. When a physician enters a particular medical problem or symptom as a search query, the search engine obtains a ranked list of keywords that are closely related (or similar) to the given search query and recommends to the physician search terms to be included in the query in order to make the search results more refined. The system will first build an index of problems, symptoms, and medications organized by identical PACS imaging study types by aggregating information from millions of PACS and EMR PHI entries. Using metadata that describe the attributes of the keywords, which is obtained from other sources, the system will build a similarity matrix that indicates the similarity score between each pair of keywords. This similarity model is precomputed and stored. When a search occurs, the entered keyword is looked up in the similarity matrix and the top similar keywords are ranked and returned.

FIG. 14 illustrates various screenshots of the current system such as the real-time collaboration tool between doctors, which assists in improving patient outcomes or can be utilized for education purposes for Resident Doctors. Beyond the core functionality of connectivity, visualization, search, search log, replay and improving physician interactions and workflows, the system aims to improve real-time collaboration between physicians. The present system can allow multiple users to comment on an image, patient data or annotate a record, such that comments with the current system providing collated and viewing in an integrated way in a chronological order or filtered by ordering doctor, imaging study type, reviewing doctor and pertinent dates. The system maintains the root content and relationships of interaction type like view, comment, annotate etc. for every patient imaging study and each user.

Physician collaboration itself may involve multi-channel like video sharing, screen sharing, chat room, annotations on the image snapshot. Each collaboration session can be stored as a transaction on the system, which can be updated to original data. Each collaboration can be created in multiple ways, auto-invite, and on-demand invite and pre-invited, utilizing any of channels like video, screens sharing or chat room based collaborating within the "Virtual Bedside" functions.

One of the most areas of contention in healthcare is computer vs. man, manifested as push back by physicians regarding the kind of technology that is being forced upon them to replace their expertise and invaluable human knowledge and compassion. The present invention's ELEIVIREX™ technology builds the Patient Provider Matrix and incorporates the world's first organic/human AI growth model in the healthcare sector. The present system, through its use, is creating a unique digital library and working interactive platform environment that utilizes knowledge physicians both contribute and are able to access to create an invaluable resource to digitally transform daily medical practice. In this way, physician input will be considered by many to not only benefit their personal practices, but be for the greater good, enticing their engagement.

ELEMREV™ use and MODL availability within the system provides doctors with the unique opportunity to learn from one another, which exponentially expands and accelerates the AI capability of the technology that crawls commonly used phrases, words to organize the commentary and provide statistical confidence to the AI, to which any additionally reviewing physician viewer can then contribute. Think of an analogy being 'ask the audience' on the TV show 'Millionaire', that quickly provides statistics to validate and identify confidence in one of 4 available answers upon which the contestant can either agree or disagree, but will make a real time decision based on voter confidence. The system amasses big data that is organized within MODL to provide similar choices with statistical confidence to treating physicians, on demand, in real time. The way the real world healthcare system functions is that there are 1.1 million fragmented skill sets and experiences isolated within each of the system's individual physicians. ELEMREV™ technology unlocks, captures and harnesses within MODL for common physician access to learn from colleagues when treating patients with difficult management issues, providing system wide access to clinical management team input and guidance for improved, more predictable patient care as a predictable pathway toward overall cost savings.

Figure 15:
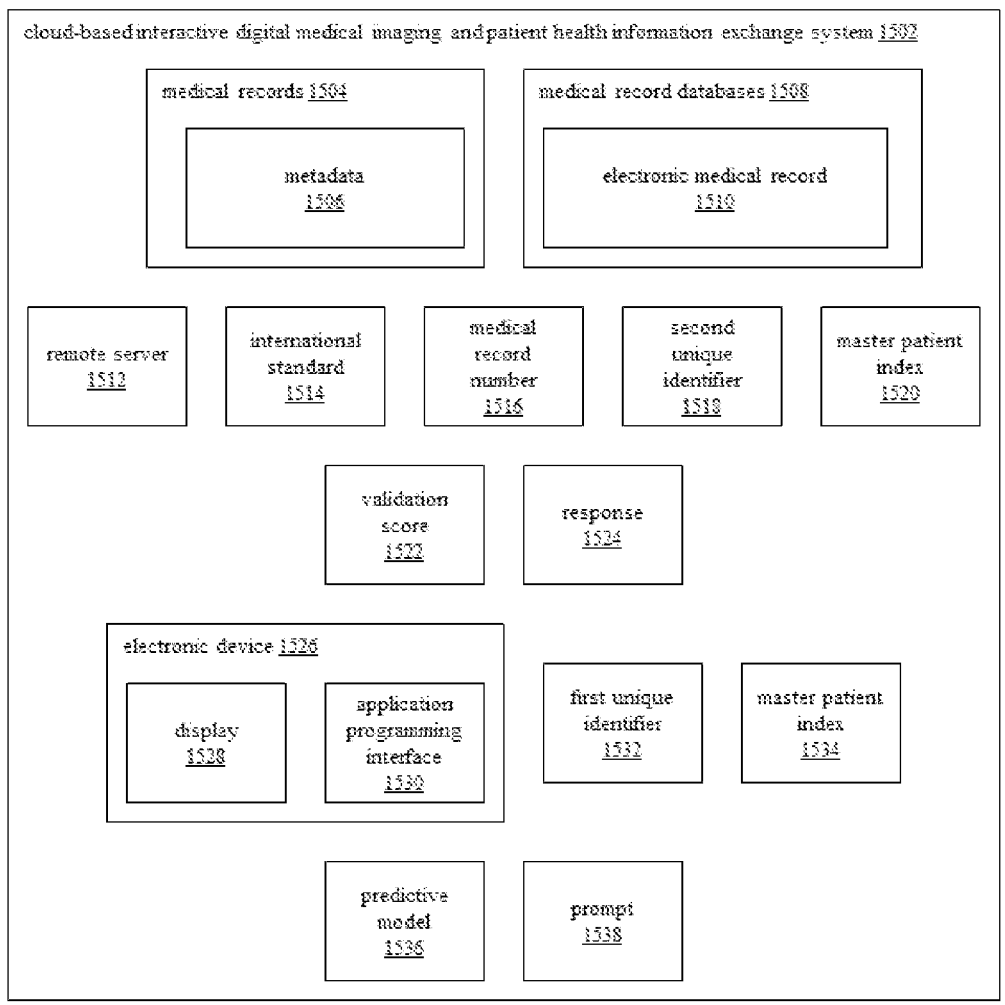
FIG. 15 is a block diagram illustrating a cloud-based interactive digital medical imaging and patient health information exchange system, according to some embodiments of the present disclosure.

FIG. 15 is a block diagram that describes a cloud-based interactive digital medical imaging and patient health information exchange system 1502, according to some embodiments of the present disclosure. In some embodiments, the cloud-based interactive digital medical imaging and patient health information exchange system 1502 may include one or more medical records 1504, one or more medical record databases 1508 retain the one or more medical records 1504, an electronic device 1526 in communication with the remote server 1512, and a master patient index 1520 (MPI) algorithm combines data from the PACS database or the EMR database.

In some embodiments, the cloud-based interactive digital medical imaging and patient health information exchange system 1502 may also include a remote server 1512, the remote server 1512 connected to the one or more medical record databases 1508 in real-time. The cloud-based interactive digital medical imaging and patient health information exchange system 1502 may also include an international standard 1514, the international standard 1514 operating at an application layer of the remote server 1512 to establish connectivity to the PACS database and the EMR database.

In some embodiments, the cloud-based interactive digital medical imaging and patient health information exchange system 1502 may also include a medical record number 1516 (MRN), the MRN may be associated with the one or more medical records 1504. The cloud-based interactive digital medical imaging and patient health information exchange system 1502 may also include a first unique identifier 1532, the first unique identifier 1532 may be based on a combination of the one or more medical records 1504 on the PACS database and the MRN.

In some embodiments, the cloud-based interactive digital medical imaging and patient health information exchange system 1502 may also include a second unique identifier 1518, the second unique identifier 1518 may be based on a combination of the one or more medical records 1504 on the EMR database and the MRN. The cloud-based interactive digital medical imaging and patient health information exchange system 1502 may also include a master patient index 1534 (MPI), the master patient index 1534 retaining the first unique identifier 1532 and the second unique identifier 1518, the MPI to identify the patient profile across the one or more medical record databases 1508.

In some embodiments, the cloud-based interactive digital medical imaging and patient health information exchange system 1502 may also include a predictive model 1536, the predictive model 1536 may be trained using the MPI algorithm. The cloud-based interactive digital medical imaging and patient health information exchange system 1502 may also include a validation score 1522, the validation score 1522 may be generated by the predictive model 1536 when the metadata 1506 of the one or more medical records 1504 may be matched for the patient profile, using the predictive model 1536, based on the first unique identifier 1532 and the second unique identifier 1518 in the MPI.

In some embodiments, the cloud-based interactive digital medical imaging and patient health information exchange system 1502 may also include a prompt 1538, the prompt 1538 may be generated by the remote server 1512 and displayed on the display 1528 of the electronic device 1526 when the validation score 1522 may be outside of a pre-defined threshold. The cloud-based interactive digital medical imaging and patient health information exchange system 1502 may also include a response 1524, the response 1524 may be generated by the remote server 1512 to indicate if the one or more medical records 1504 may be associated with the patient profile or if the one or more medical records 1504 may be not associated with the patient profile.

In some embodiments, the one or more medical records 1504 may include metadata 1506. The one or more medical record databases 1508 may include an electronic medical record 1510 (EMR) database. A picture archiving and communicating systems (PACS) database. The electronic device 1526 may include a display 1528 and an application programming interface 1530 (API). The one or more medical records 1504 may be displayed on the API from the PACS database and the EMR database.

In some embodiments, the MRN may be configured to link a patient profile on both the PACS database and the EMR database. The metadata 1506 of the one of more medical records may be extracted, using the predictive model 1536. Responsive to the generated prompt, the one or more medical records 1504 of the patient profile may be displayed on the display 1528 of the electronic device 1526 based on the first unique identifier 1532 and the second unique identifier 1518 in real-time.

In some embodiments, the remote server 1512, when connecting to the PACS database and the EMR database, may be further configured to establish an application layer connectivity utilizing Health Level 7 (HL7) or Fast Healthcare Interoperability Resources (FHIR) and Digital Imaging and Communications in Medicine (DICOM) for imaging. In some embodiments, the one or more medical records 1504 may include medical imaging records.

In some embodiments, a database of the multiple databases. In some embodiments, the physician database to monitor activity of the physician database using the predictive model 1536 via artificial intelligence. In some embodiments, the international standard 1514 may be a health level 7 (HL7) international standard for healthcare data exchange. In some embodiments, the international standard 1514 may be fast healthcare interoperability resources (FHIR) for healthcare data exchange. In some embodiments, the international standard 1514 may be digital imaging and communications in medicine (DICOM) for medical imaging exchange. In some embodiments, the MPI algorithm may be a heuristics based matching algorithm.

Figure 16:
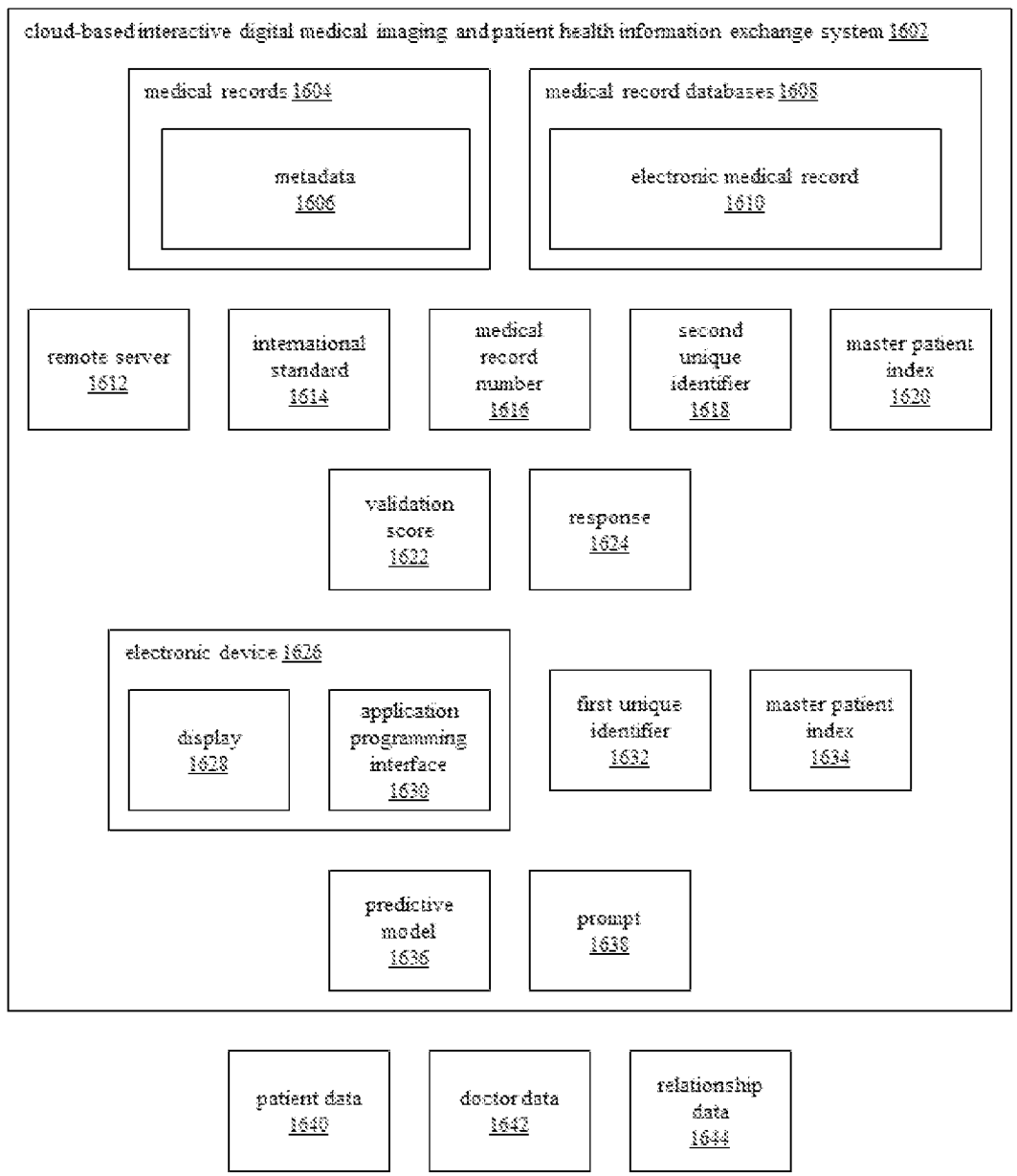
FIG. 16 is a block diagram further illustrating the cloud-based interactive digital medical imaging and patient health information exchange system from FIG. 15, according to some embodiments of the present disclosure.
Figure 17:
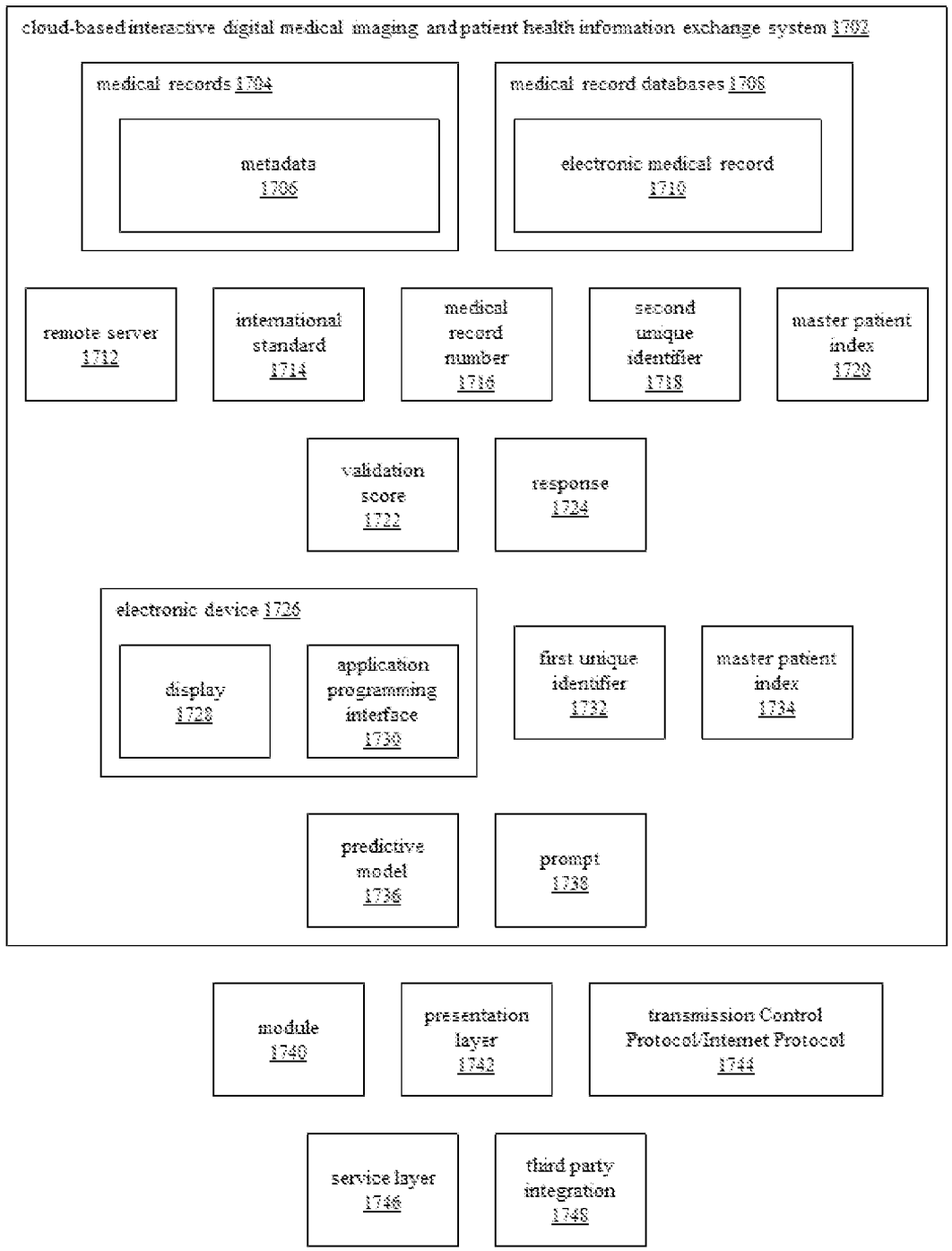
FIG. 17 is a block diagram further illustrating the cloud-based interactive digital medical imaging and patient health information exchange system from FIG. 15, according to some embodiments of the present disclosure.
Figure 18A:
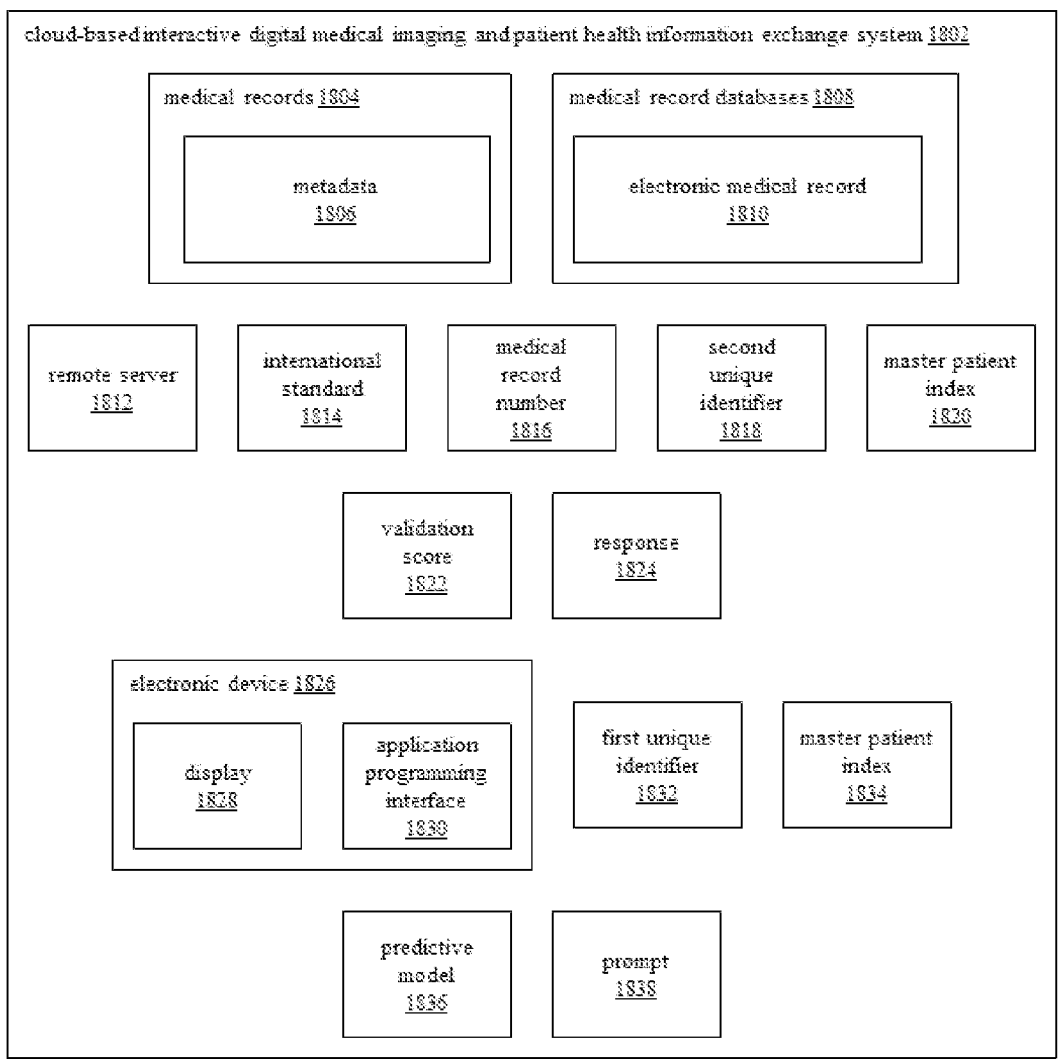
FIG. 18A is a block diagram further illustrating the cloud-based interactive digital medical imaging and patient health information exchange system from FIG. 15, according to some embodiments of the present disclosure.
Figure 18B:
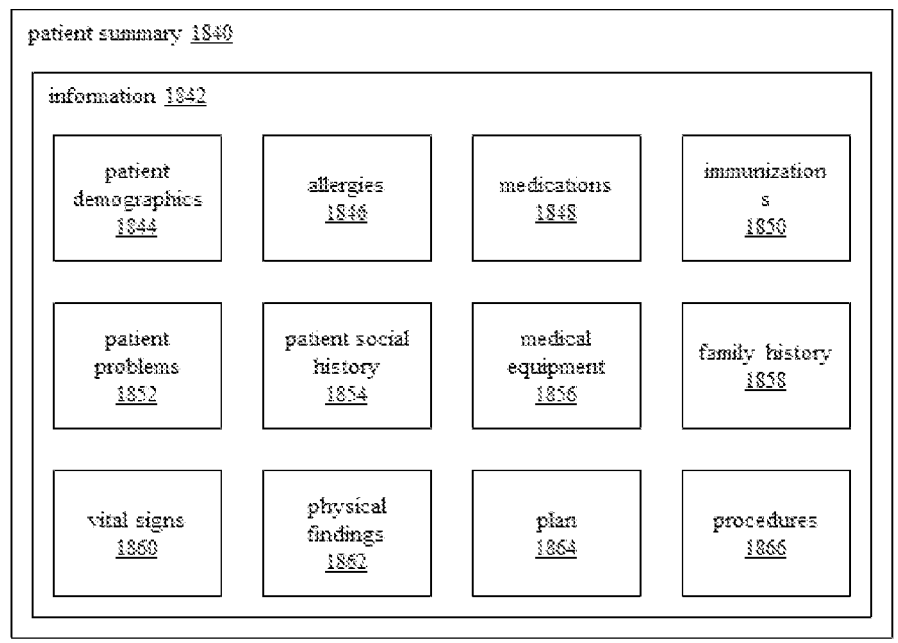
FIG. 18B is a block diagram extending from FIG. 18A and further illustrating the cloud-based interactive digital medical imaging and patient health information exchange system, according to some embodiments of the present disclosure.

FIG. 16 is a block diagram that further describes the cloud-based interactive digital medical imaging and patient health information exchange system 1502 from FIG. 15, according to some embodiments of the present disclosure. In some embodiments, the system 1502 may use the processor to index one or more medical records with data selected from the group. FIG. 17 is a block diagram that further describes the cloud-based interactive digital medical imaging and patient health information exchange system 1502 from FIG. 15, according to some embodiments of the present disclosure.

FIGS. 18A to 28B are block diagrams that further describe the cloud-based interactive digital medical imaging and patient health information exchange system 1502 from FIG. 15, according to some embodiments of the present disclosure. In some embodiments, the system 1502 may include. In some embodiments, the patient summary 1840 may include information 1842 selected from the group. The information 1842 may include patient demographics 1844, allergies 1846, medications 1848, immunizations 1850, patient problems 1852, patient social history 1854, medical equipment 1856, family history 1858, vital signs 1860, physical findings 1862, plan 1864 of care, and procedures 1866. Encounters (not shown) and Results (not shown).

In an embodiment, this system framework may include a presentation layer, service layer, transmission Control Protocol/Internet Protocol (TCP/IP), and third-party integration. The presentation layer offers guidance on displaying, modifying, and interacting with the diverse user controls within a customized module. This module will then communicate with the service layer using HTTPS. This software architecture may include several distinct layers and components. A presentation layer is responsible for how information is displayed to the user. It manages the user interface, including things such as buttons, forms, and/or other controls. In this context, a presentation layer explains how to display, modify, and interact with user controls within a custom module.

In an embodiment, the foundation or physical architecture of this system may include Azure Cloud-run Services for constructing and deploying services. Utilizing Function apps, robust web applications may be developed that autonomously adjust their scale, operate in a highly accessible setup, and/or demand minimal administrative effort for tasks like scalability and backups. In the Operations Environment, there is a centralized gateway to access the infrastructure. It encompasses many the services frequently employed by the operations team for overseeing and supervising the infrastructure.

In an embodiment, various environments may be configured for code deployment. For example, the production environment prioritizes security and reliability. Production-grade components may be employed in this environment. The databases in production are configured with failover clustering across different zones, ensuring high availability. In the event of a failure in one zone, the other zone serves as a failover option. In another example, the staging environment is tailored for fundamental integration testing and utilizes hardware with development-grade components. On the other hand, the development environment is specifically for application development and unit testing, employing hardware with development-grade components.

In an embodiment, a service layer handles the underlying logic and operations of the software. It processes requests, performs operations, and communicates with other parts of the application. In this case, the service layer lay interacts with the presentation layer using HTTPs, which is a secure communication protocol over the internet. TCP/IP is a set of rules governing how data packets are sent, received, and processed over networks, including the internet. It's a fundamental protocol for communication between devices on a network. For example, Azure Functions is a serverless solution that allows a user to write less code, reduce infrastructure maintenance, and/or cut costs. A function app enables a user to group functions together for easier management, deployment, scaling, and resource sharing. The configuration will be Elastic Premium, and the operating system will be Windows. API Management serves as an API gateway, positioned in front of the HTTP function. It may be utilized for publishing and overseeing APIs that are utilized by client applications. Employing a gateway helps to separate the front-end application from the back-end APIs. For instance, API Management may reconfigure URLs, alter requests before they reach the back end, define request or response headers, and/or perform similar operations. API Management may additionally serve to address overarching considerations including: Enforcing usage quotas and rate limits, Facilitating cross-origin requests (CORS), Storing responses in a cache, and Monitoring and recording requests.

In an embodiment, Azure Monitor may be used to gather performance metrics regarding the Azure services implemented in the solution. By visualizing these metrics on a dashboard, a user may gain insight into the solution's overall health. Additionally, it compiles application logs. Azure Database for MySQL streamlines application development by handling time-consuming database management tasks including, but not limited to, backups, software updates, monitoring, scaling, and/or replication.

In an embodiment, a resource group serves as a container that encompasses related resources for the Azure solution. It may encompass many resources for the solution and/or predetermined resources a user wishes to manage as a group. A user may have the flexibility to allocate resources to resource groups according to your organizational needs. The resource group holds metadata about the resources. Therefore, when a user specifies a location for the resource group, it is indicating where that metadata is stored.

In an embodiment, user roles may be performed by many individuals. In an example. a patient is an individual who may securely share their medical documents with a physician and request expert opinions after authenticating themselves within the application. A minor is an individual who may register with the application under parental supervision. A physician is a qualified medical professional who can authenticate patient documents, provide medical opinions, seek opinions from other physicians, and be designated as an expert in one or more specialties for a Center of Excellence (COE). An admin is an authorized user who can verify patient documents, provide medical opinions, seek opinions from other physicians, and act on behalf of another physician. Admins can only log in when invited by another user.

In an embodiment, a 3rd Party Integration may indicate that the software interacts with external components or services developed by third-party entities. These may be libraries, APIs, or other software tools that enhance or extend the functionality of the application. For example, Google's Captcha service, through its API, can be employed to confirm whether a user is a human or a robot. SendGrid, a cloud-based SMTP provider, facilitates email sending without the need to manage email servers. Twilio offers programmable messaging capabilities, enabling the sending of SMS messages.

If a public authentication page is present, it is desirable to implement and activate captcha services. Regarding data encryption, several steps may be followed. This includes categorizing data processed, stored, and/or transmitted by the application, ensuring that any sensitive information adheres to privacy laws, regulatory requirements, or pertinent business needs, and subsequently undergoes encryption. Sensitive data may not be retained unnecessarily and may be promptly removed. It is desirable to have modern and robust standard algorithms, protocols, and keys in place. Data in transit may be encrypted using secure protocols such as TLS, incorporating forward secrecy (FS) ciphers, cipher prioritization by the server, and/or secure parameters. Responses containing sensitive data may have caching disabled. Outdated protocols such as FTP or SMTP may not be used for transporting sensitive information. Passwords may be stored using strong adaptive and salted hashing functions, considering a work factor to bolster security. It is desirable to consistently employ authenticated encryption rather than relying solely on encryption. Keys may be generated in a cryptographically random manner and stored in memory as byte arrays. In the event a password is used, it may be transformed into a key through an appropriate password-based key derivation function. It is desirable to refrain from using deprecated cryptographic functions and padding schemes.

Broken Access Control involves taking specific measures on the server-side code or serverless API. These measures include employing a "deny by default" approach for all resources except public ones. Access control mechanisms may be implemented consistently across the application, with an emphasis on minimizing Cross-Origin Resource Sharing (CORS) usage. It's desirable to ensure that access controls enforce record ownership, rather than assuming that a user may perform any action on a record. Additionally, unique application business limit requirements may be enforced through domain models. It's imperative to disable web server directory listing and ensure that file metadata and backup files remain inaccessible within web roots. Logging instances of access control failures and promptly notifying administrators when inappropriate access is detected is essential. Lastly, stateful session identifiers may be invalidated on the server after a user logs out.

To prevent injection attacks, it's advised to prioritize using a secure API that bypasses the interpreter entirely, provides a parameterized interface, or migrates to Object Relational Mapping Tools (ORMs). Implementing positive or "whitelist" server-side input validation is also desirable. For any remaining dynamic queries, special characters may be escaped using the specific escape syntax for that interpreter. Additionally, using LIMIT and other SQL controls within queries may help prevent mass disclosure of records in case of SQL injection.

To address identification and authentication failures, it's recommended to implement multi-factor authentication to thwart automated credential stuffing, brute force, and stolen credential reuse attacks. Default credentials, particularly for admin users, may not be shipped or deployed. Implementing weak password checks, such as screening new or modified passwords against a list of common weak passwords, is advised. Password length, complexity, and rotation policies may be aligned with best practices. Strengthening registration, credential recovery, and API pathways against account enumeration attacks by using consistent messages for all outcomes is desirable. Implementing limitations or increasing delays for failed login attempts (taking care not to create a denial of service situation), and logging all failures while promptly alerting administrators of any detected credential stuffing, brute force, or other attacks is also important. Employing a server-side, secure, built-in session manager that generates a new random session ID with high entropy after login is essential. The session identifier may not be included in the URL, may be securely stored, and invalidated after logout, idle, and absolute timeouts.

To address security logging and monitoring failures, it's important to ensure that all login, access control, and server-side input validation failures are logged with sufficient user context for identifying suspicious or malicious accounts. These logs may be retained for an adequate duration to allow delayed forensic analysis. Generating logs in a format that may be easily consumed by log management solutions is advised. Additionally, ensuring that log data is correctly encoded to prevent injections or attacks on the logging or monitoring systems is desirable. Implementing audit trails with integrity controls for high-value transactions, such as using append-only database tables or similar measures, is also recommended.

Regarding Server-Side Request Forgery, from the Network Layer, it's advised to segment remote resource access functionality into separate networks to mitigate the impact of SSRF. Enforcing a "deny by default" approach with firewall policies or network access control rules to block all non-essential intranet traffic is desirable. From the Application Layer, it's important to sanitize and validate all client-supplied input data. Enforcing the URL schema, port, and destination with a positive allow list is recommended. Avoiding sending raw responses to clients and disabling HTTP redirections are also important measures. Being mindful of URL consistency to prevent attacks like DNS rebinding and "time of check, time of use" (TOCTOU) race conditions is advised.

In an embodiment, options in the application may be stored in Azure Application Insights, providing a comprehensive record of caught exceptions. Additionally, various metrics may be generated based on recorded errors, including unauthenticated logins, internal server errors, CPU usage, and memory usage. Alarms have been configured to send email alerts based on these metrics, covering high CPU and memory usage, high database server utilization, and service downtime. Centralized Logging is facilitated through the use of the Function Monitor for efficient log checking. Different log levels, including debug, critical, error, informational, and verbose, may be specified for comprehensive logging. Log modes include file storage and console logging. A custom logging class with its constructors is implemented, allowing for structured logging with specified parameters such as class name, method name, log level, and message.

Error Handling is a fundamental aspect of the web application, with standard error-handling methods systematically implemented throughout. This includes handling all unhandled exceptions, specifically those with HTTP status codes 500, 502, and 504. Security Measures: Security is paramount in the development of this system. Several measures have been taken to ensure robust security: Authentication: Rigorous authentication processes may be in place to verify user identities.

SSL Encryption: All server communications may be secured using 128-bit SSL encryption, safeguarding data in transit. Cryptography: Personal data transferred via API requests and responses is encrypted using AES 256 encryption, adding an extra layer of protection. Exception Management: Standardized exception handling methods may be implemented to manage unexpected situations. Complex Password Policy: A policy for creating complex passwords, along with regular password changes, is enforced to enhance security. Encrypt Data in Transit: Data packets sent to and received from the server may be protected using 128-bit SSL encryption, preventing tampering or analysis. Login Security: Measures may be in place to limit the number of incorrect password attempts, thwarting brute force attacks. OTP Security: One-time passwords (OTPs) may be verified on the server to ensure security, with specific criteria for OTP format and attempt limits.

Forgot Password: Stringent measures may be taken to prevent abuse of the "forgot password" feature, including limiting incorrect entries and encrypting returned information. Local Data Security: Local data is stored in encrypted form to prevent unauthorized access and leakage of information. App System Security: Activities like preventing code decompilation, ensuring device integrity, and securing source code may be performed to bolster system security. HTTPS Host Name Authentication Security: Host names may be explicitly verified to prevent trust in potentially malicious hostnames. Denial of Service Attacks: Various steps may be taken to minimize the impact of potential denial of service attacks, including setting non-exported components and capturing exceptions during intent processing. Debugging Risk: Debugging capabilities may be managed, with debuggable properties set to false and anti-debugging measures implemented. Web Application Security: A range of security measures may be implemented to ensure the web application is free from vulnerabilities. These measures include domain email spoofing protection, SPF, DKIM, and DMARC record configuration, Content Security Policy implementation, secure flag marking for cookies, HTTPOnly flag marking for cookies, and suppression of server software may be information headers.

Logging and Exception Handling: In the application, exceptions may be logged and stored in Azure Application Insights, providing a comprehensive record of caught exceptions. Alongside this, various metrics may be generated based on recorded errors, encompassing unauthenticated logins, internal server errors, CPU usage, and memory usage. Additionally, alarms have been set up to send email alerts in response to specific metrics, covering instances of high CPU and memory usage, elevated database server utilization, and service downtime.

Centralized Logging is facilitated through the use of the Function Monitor, ensuring efficient log checking. It allows for different log levels, including debug, critical, error, informational, and verbose, to be specified for comprehensive logging. Log modes, which include file storage and console logging, may be also configured. A custom logging class, complete with its constructors, is implemented, enabling structured logging with specified parameters such as class name, method name, log level, and message. Error Handling is fundamentally important in the web application, with standard error-handling methods systematically implemented throughout. This includes addressing all unhandled exceptions, specifically those with HTTP status codes 500, 502, and 504.

Security Measures: Security holds paramount importance in the development of this system, and several measures have been put in place to ensure robust security. Authentication processes may be rigorous, verifying user identities. Server communications may be safeguarded using 128-bit SSL encryption, ensuring the security of data in transit. Personal data transferred via API requests and responses is encrypted using AES 256 encryption, adding an extra layer of protection. Standardized exception handling methods may be implemented to effectively manage unexpected situations. A policy for creating complex passwords, along with regular password changes, is enforced to enhance security. Data packets sent to and received from the server may be protected using 128-bit SSL encryption, preventing tampering or analysis. Measures may be in place to limit the number of incorrect password attempts, thwarting brute force attacks. One-time passwords (OTPs) may be verified on the server to ensure security, with specific criteria for OTP format and attempt limits. Stringent measures may be taken to prevent abuse of the "forgot password" feature, including limiting incorrect entries and encrypting returned information. Local data is stored in encrypted form to prevent unauthorized access and leakage of information. Activities like preventing code decompilation, ensuring device integrity, and securing source code may be performed to bolster system security. Host names may be explicitly verified to prevent trust in potentially malicious hostnames.

Various steps may be taken to minimize the impact of potential denial of service attacks, including setting non-exported components and capturing exceptions during intent processing. Debugging capabilities may be managed, with debuggable properties set to false and anti-debugging measures implemented. A range of security measures may be implemented to ensure the web application is free from vulnerabilities. These measures include domain email spoofing protection, SPF, DKIM, and DMARC record configuration, Content Security Policy implementation, secure flag marking for cookies, HTTP Only flag marking for cookies, and suppression of server software be information headers.

When introducing elements of the present disclosure or the embodiment(s) thereof, the articles "a," "an," and "the" may be intended to mean that there may be one or more of the elements. Similarly, the adjective "another," when used to introduce an element, is intended to mean one or more elements. The terms "including" and "having" may be intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A cloud-based interactive digital medical imaging and patient health information exchange system for gathering and indexing medical records housed on multiple databases, the system comprising:
   one or more medical records having metadata;
   one or more medical record databases retain the one or more medical records, the one or more medical record databases comprising:
   a picture archiving and communicating systems (PACS) database; and an electronic medical record (EMR) database;
a remote server, the remote server connected to the one or more medical record databases in real-time;
an international standard, the international standard operating at an application layer of the remote server to establish connectivity to the PACS database and the EMR database;
an electronic device in communication with the remote server, the electronic device having a display and an application programming interface (API), and
wherein the one or more medical records is displayed on the API from the PACS database and the EMR database;
a medical record number (MRN), the MRN is associated with the one or more medical records, wherein the MRN is configured to link a patient profile on both the PACS database and the EMR database;
a first unique identifier, the first unique identifier is based on a combination of the one or more medical records on the PACS database and the MRN;
a second unique identifier, the second unique identifier is based on a combination of the one or more medical records on the EMR database and the MRN;
a master patient index (MPI), the master patient index retaining the first unique identifier and the second unique identifier, the MPI to identify the patient profile across the one or more medical record databases;
a master patient index (MPI) algorithm combines data from the PACS database or the EMR database;
a predictive model, the predictive model is trained using the MPI algorithm, and
wherein the metadata of the one of more medical records is extracted, using the predictive model;
a validation score, the validation score is generated by the predictive model when the metadata of the one or more medical records is matched for the patient profile, using the predictive model, based on the first unique identifier and the second unique identifier in the MPI;
a prompt, the prompt is generated by the remote server and displayed on the display of the electronic device when the validation score is outside of a predefined threshold, and
wherein responsive to the generated prompt, the one or more medical records of the patient profile is displayed on the display of the electronic device based on the first unique identifier and the second unique identifier in real-time; and
a response, the response is generated by the remote server to indicate if the one or more medical records may be associated with the patient profile or if the one or more medical records is not associated with the patient profile.

2. The system as recited in claim 1, wherein the remote server, when connecting to the PACS database and the EMR database, is further configured to establish an application layer connectivity utilizing Health Level 7 (HL7) or Fast Healthcare Interoperability Resources (FHIR) and Digitial Imaging and Communications in Medicine (DICOM) for imaging.

3. The system as recited in claim 1, further comprising one or more memory storage mediums, configured to store the metadata.

4. The system as recited in claim 1, wherein the system uses the processor to index one or more medical records with data selected from the group consisting of: patient data; doctor data; and relationship data.

5. The system as recited in claim 1, wherein the one or more medical records includes medical imaging records.

6. The system as recited in claim 1, further comprising:
a module comprising:
a presentation layer;
a service layer;
a transmission Control Protocol/Internet Protocol (TCP/IP); and
a third party integration.

7. The system as recited in claim 1, further comprising:
a patient summary of the patient profile.

8. The system as recited in claim 7, wherein the patient summary includes information selected from the group consisting of: patient demographics; allergies; medications; immunizations; patient problems; patient social history; medical equipment; family history; vital signs; physical findings;
encounters; plan of care; procedures; and results.

9. The system as recited in claim 1, further comprising medical commentary for the patient portfolio, the medical commentary to be saved to the indexed one or more medical records.

10. The system as recited in claim 1, wherein a database of the multiple databases comprise a physician database.

11. The system as recited in claim 10, wherein the physician database to monitor activity of the physician database using the predictive model via artificial intelligence.

12. The system as recited in claim 1, wherein the international standard is a health level 7 (HL7) international standard for healthcare data exchange.

13. The system as recited in claim 1, wherein the international standard is fast healthcare interoperability resources (FHIR) for healthcare data exchange.

14. The system as recited in claim 1, wherein the international standard is digital imaging and communications in medicine (DICOM) for medical imaging exchange.

15. The system as recited in claim 1, wherein the MPI algorithm is a heuristics based matching algorithm.

* * * * *